United States Patent
Albert et al.

(10) Patent No.: US 9,920,045 B2
(45) Date of Patent: Mar. 20, 2018

(54) SOLID STATE FORMS OF A PDE10 INHIBITOR

(71) Applicant: Omeros Corporation, Seattle, WA (US)

(72) Inventors: Ekaterina Albert, West Lafayette, IN (US); Jennifer Leigh Nelson, Kokomo, IN (US); Christopher Scott Seadeek, West Lafayette, IN (US); Karl Reineke, Niskayuna, NY (US); Marco Jonas, Cohoes, NY (US); Suba Iyer, Albany, NY (US); Xufeng Sun, Albany, NY (US); Neil S. Cutshall, Snohomish, WA (US); Jennifer Lynn Gage, Kenmore, WA (US); Thomas L. Little, Seattle, WA (US); Wayne Douglas Luke, West Lafayette, IN (US); Elisabeth C. A. Brot, Albany, NY (US); Michael James McDermott, Clifton Park, NY (US)

(73) Assignee: Omeros Corporation, Seattle, WA (US)

( * ) Notice: Subject to any disclaimer, the term of this patent is extended or adjusted under 35 U.S.C. 154(b) by 0 days.

(21) Appl. No.: 15/344,372

(22) Filed: Nov. 4, 2016

(65) Prior Publication Data

US 2017/0166559 A1    Jun. 15, 2017

Related U.S. Application Data

(60) Provisional application No. 62/251,074, filed on Nov. 4, 2015.

(51) Int. Cl.
  *C07D 417/10*    (2006.01)

(52) U.S. Cl.
  CPC ........ *C07D 417/10* (2013.01); *C07B 2200/13* (2013.01)

(58) Field of Classification Search
  CPC .................................................. C07D 417/10
  See application file for complete search history.

(56) References Cited

U.S. PATENT DOCUMENTS

| | | |
|---|---|---|
| 5,693,652 A | 12/1997 | Takase et al. |
| 6,177,154 B1 | 1/2001 | Matsui et al. |
| 6,197,901 B1 | 3/2001 | Rohde et al. |
| 6,403,805 B1 | 6/2002 | Freyne et al. |
| 7,053,192 B2 | 5/2006 | Li et al. |
| 7,129,238 B2 | 10/2006 | Banner et al. |
| 7,449,486 B2 | 11/2008 | Hans et al. |
| 7,786,139 B2 | 8/2010 | Bergmann et al. |
| 8,278,327 B2 | 10/2012 | Bergmann et al. |
| 8,343,970 B2 | 1/2013 | Cutshall et al. |
| 8,377,930 B2 | 2/2013 | Cutshall et al. |
| 8,420,655 B2 | 4/2013 | Chen et al. |
| 8,685,975 B2 | 4/2014 | Cutshall et al. |
| 9,102,643 B2 | 8/2015 | Cutshall et al. |
| 9,434,707 B2 | 9/2016 | Cutshall et al. |
| 9,493,447 B2 | 11/2016 | Cutshall et al. |
| 2003/0032579 A1 | 2/2003 | Lebel et al. |
| 2005/0135999 A1 | 6/2005 | Elomari et al. |
| 2006/0074102 A1 | 4/2006 | Cusack et al. |
| 2006/0128695 A1 | 6/2006 | Bourguignon et al. |
| 2007/0032435 A1 | 2/2007 | Alani et al. |
| 2007/0032531 A1 | 2/2007 | Smith et al. |
| 2007/0249544 A1 | 10/2007 | Himmelsbach et al. |
| 2008/0004448 A1 | 1/2008 | Wayne et al. |
| 2008/0089835 A1 | 4/2008 | Burton |
| 2008/0090834 A1 | 4/2008 | Hoover et al. |
| 2008/0103186 A1 | 5/2008 | Glover et al. |
| 2008/0139569 A1 | 6/2008 | Rocco et al. |
| 2008/0319024 A1 | 12/2008 | Greil et al. |
| 2009/0069281 A1 | 3/2009 | Austad et al. |
| 2009/0124652 A1 | 5/2009 | Ach et al. |
| 2009/0137794 A1 | 5/2009 | Mendez et al. |
| 2009/0176829 A1 | 7/2009 | Verhoest et al. |
| 2009/0176983 A1 | 7/2009 | Dova et al. |
| 2009/0203705 A1 | 8/2009 | Biagetti et al. |
| 2009/0221586 A1 | 9/2009 | Okada et al. |
| 2009/0239946 A1 | 9/2009 | McKeown et al. |
| 2010/0021539 A1 | 1/2010 | Kowalski et al. |
| 2010/0035887 A1 | 2/2010 | Ricciardi |
| 2013/0137707 A1 | 5/2013 | Cox et al. |
| 2013/0158081 A1 | 6/2013 | Almstead et al. |
| 2016/0024069 A1 | 1/2016 | Cutshall et al. |
| 2017/0022190 A1 | 1/2017 | Gage et al. |

FOREIGN PATENT DOCUMENTS

| | | |
|---|---|---|
| DE | 43 23 192 A1 | 1/1995 |
| DE | 43 25 846 C1 | 1/1995 |
| DE | 43 43 286 A1 | 6/1995 |
| EP | 1 568 691 A1 | 8/2005 |

(Continued)

OTHER PUBLICATIONS

Aggarwal et al., "A Novel One-Pot Method for the Preparation of Pyrazoles by 1,3-Dipolar Cycloadditions of Diazo Compounds Generated in Situ," *J. Org. Chem.* 68(13):5381-5383, 2003.
Background Information for the Oct. 2002 ACPS Meeting, "Scientific Considerations of Polymorphism in Pharmaceutical Solids: Abbreviated New Drug Applications," URL= http://www.fda.gov/ohrms/dockets/ac/02/briefing/3900B1_04_polymorphism.htm, download date Jan. 25, 2006, 5 pages.
Banker et al. (eds.), *Modern Pharmaceutics: Third Edition, Revised and Expanded*, Marcel Dekker, New York, USA, 1996, pp. 596. (2 pages).
Decision on Appeal, In re Appeal 2010-010445, issued Aug. 5, 2011, for U.S. Appl. No. 10/693,315, Ex parte Takao et al., 17 pages.
Dias et al., "Synthesis and analgesic properties of 5-acyl-arylhydrazone 1-H pyrazolo [3,4-b] pyridine derivatives," *Pharmaceutics Acta Helvetiae* 69:163-169, 1994.

(Continued)

*Primary Examiner* — Matthew P Coughlin
(74) *Attorney, Agent, or Firm* — Seed IP Law Group LLP

(57) ABSTRACT

The invention relates to a novel variable hydrate crystalline form of 1-(5-(4-chloro-3,5-dimethoxyphenyl)furan-2-yl)-2-ethoxy-2-(4-(5-methyl-1,3,4-thiadiazol-2-yl)phenyl)ethanone, methods for the preparation thereof, pharmaceutical compositions thereof and their use in the inhibition of PDE10.

18 Claims, 28 Drawing Sheets

(56) References Cited

FOREIGN PATENT DOCUMENTS

| | | |
|---|---|---|
| WO | 92/01679 A1 | 2/1992 |
| WO | 94/12461 A1 | 6/1994 |
| WO | 96/00218 A1 | 1/1996 |
| WO | 96/15096 A1 | 5/1996 |
| WO | 96/31485 A1 | 10/1996 |
| WO | 96/31486 A1 | 10/1996 |
| WO | 96/41609 A2 | 12/1996 |
| WO | 97/27190 A1 | 7/1997 |
| WO | 98/08830 A1 | 3/1998 |
| WO | 99/45914 A1 | 9/1999 |
| WO | 00/34254 A1 | 6/2000 |
| WO | 00/55139 A2 | 9/2000 |
| WO | 01/41807 A2 | 6/2001 |
| WO | 01/44226 A1 | 6/2001 |
| WO | 01/96334 A2 | 12/2001 |
| WO | 2004/011410 A1 | 2/2004 |
| WO | 2004/033652 A2 | 4/2004 |
| WO | 2004/058254 A1 | 7/2004 |
| WO | 2004/071509 A1 | 8/2004 |
| WO | 2004/094411 A1 | 11/2004 |
| WO | 2005/103022 A1 | 11/2005 |
| WO | 2006/072828 A2 | 7/2006 |
| WO | 2006/084186 A2 | 8/2006 |
| WO | 2006/116355 A1 | 11/2006 |
| WO | 2007/058338 A2 | 5/2007 |
| WO | 2007/073299 A1 | 6/2007 |
| WO | 2008/031014 A1 | 3/2008 |
| WO | 2008/040669 A2 | 4/2008 |
| WO | 2008/064342 A2 | 5/2008 |
| WO | 2009/010156 A2 | 1/2009 |
| WO | 2009/049022 A1 | 4/2009 |
| WO | 2009/143178 A2 | 11/2009 |
| WO | 2009/152825 A1 | 12/2009 |
| WO | 2010/017236 A1 | 2/2010 |
| WO | 2011/112828 A1 | 9/2011 |
| WO | 2014/152135 A1 | 9/2014 |

OTHER PUBLICATIONS

Enders et al., "N-heterocyclic carbene catalysed asymmetric cross-benzoin reactions of heteroaromatic aldehydes with trifluoromethyl ketones," *Chem. Commun.* 46(34):6282-6284, 2010.

Fraga et al., "Synthesis and pharmacological evaluation of novel heterotricyclic acylhydrazone derivatives, designed as PAF antagonists," *European Journal of Pharmaceutical Sciences* 11:285-290, 2000.

Fujishige et al., "Cloning and Characterization of a Novel Human Phosphodiesterase That Hydrolyzes Both cAMP and cGMP (PDE10A)," *The Journal of Biological Chemistry* 274(26):18438-18445, 1999. (9 pages).

Good et al., "The Synthesis of Oxazolo[3,2-α]pyridinium Salts," *J. Chem. Soc.* 14:1938-1945, 1970.

Hashmi et al., "Bisphenols from Furfurals by Organocatalysis and Gold Catalysis," *SYNLETT* 11:1747-1752, 2007.

Hashmi et al., "Gold Catalysis: Desymmetrization in the Furan—Yne Reaction," *SYNTHESIS* 13:2297-2307, 2010.

International Preliminary Report on Patentability, dated Sep. 18, 2012, for International Application No. PCT/US2011/027927, 7 pages.

International Search Report and Written Opinion, dated Apr. 29, 2011, for International Application No. PCT/US2011/027927, 9 pages.

International Search Report and Written Opinion, dated Jul. 13, 2015, for International Application No. PCT/US2015/027647, 17 pages.

International Search Report and Written Opinion, dated Jul. 21, 2015, for International Application No. PCT/US2015/027645, 17 pages.

International Search Report and Written Opinion, dated Sep. 14, 2016, for International Application No. PCT/US2016/028973, 10 pages.

Kamitori et al., "Convenient Synthesis of 5-Trifluoromethyl-3-Oxazolines and 5-Trifluoromethyloxazoles," *Heterocycles* 34(5):1047-1054, 1992.

Lee et al., "Discotic liquid crystalline materials for potential non-linear optical applications: Synthesis and liquid crystalline behavior of 1,3,5-triphenyl-2,4,6-triazine derivatives containing achiral and chiral alkyl chains at the periphery," *Tetrahedron Letters* 45:1019-1022, 2004.

Loughney et al., "Isolation and characterization of PDE10A, a novel human 3', 5'-cyclic nucleotide phosphodiesterase," *Gene* 234:109-117, 1999.

Lugnier, "Cyclic nucleotide phosphodiesterase (PDE) superfamily: A new target for the development of specific therapeutic agents," *Pharmacology & Therapeutics* 109(3):366-398, 2006.

Okamoto et al., "Chiral HPLC for efficient resolution of enantiomers," *Chem. Soc. Rev.* 37:2593-2608, 2008.

Olin et al., "Synthesis of 4-phenylthiazole-2-methanol and some of its derivatives. VIII," *J. [Am.] Chem. Soc.* 53:1470-1473, 1931.

Pirrung et al., "Multicomponent Reactions of Convertible Isonitriles," *J. Org. Chem.* 74(11):4110-4117, 2009.

PUBCHEM, Substance Record for SID 125300724, Nov. 10, 2011, URL=https://pubchem.ncbi.nlm.nih.gov/substance/125300724, download date Aug. 10, 2016, 5 pages.

Rodríguez-Spong et al., "General principles of pharmaceutical solid polymorphism: a supramolecular perspective," *Advanced Drug Delivery Reviews* 56:241-274, 2004.

Soderling et al., "Isolation and characterization of a dual-substrate phosphodiesterase gene family: PDE10A," *Proc. Natl. Acad. Sci. USA* 96:7071-7076, 1999.

Soderling et al., "Regulation of cAMP and cGMP signaling: new phosphodiesterases and new functions," *Current Opinion in Cell biology* 12:174-179, 2000.

Tanaka et al., "Inhibitors of Acyl-CoA:Cholesterol O-Acyltransferase. 2. Identification and Structure—Activity Relationships of a Novel Series of N-Alkyl-N-(heteroaryl-substituted benzyl)-N'-arylureas," *J. Med. Chem.* 41(13):2390-2410, 1998.

Thompson et al., "Multiple Cyclic Nucleotide Phosphodiesterase Activities from Rat Brain," *Biochemistry* 10(2):311-316, 1971.

Wilson et al., "Emerging Biology of PDE10A," *Current Pharmaceutical Design* 21(00):1-11, 2015.

Wolff (ed.), *Burger's Medicinal Chemistry and Drug Discovery*, 5th ed, vol. I: Principles and Practice, John Wiley & Sons, New York, USA, 1995, pp. 975-977. (4 pages).

Zafrani et al, "Diethyl bromodifluoromethylphosphonate: a highly efficient and environmentally benign difluorocarbene precursor," *Tetrahedron* 65:5278-5283, 2009.

SOLID STATE FORMS OF A PDE10 INHIBITOR

CROSS-REFERENCE TO RELATED APPLICATIONS

This application claims the benefit under 35 U.S.C. § 119(e) of U.S. Provisional Patent Application No. 62/251,074, filed Nov. 4, 2015, which application is incorporated herein by reference in its entirety.

BACKGROUND

Technical Field

This invention is directed to a novel variable hydrate crystalline form of Compound (I) as described herein, methods for the preparation thereof, pharmaceutical compositions thereof, and their use as a PDE10 inhibitor.

Description of the Related Art

Compound (I), 1-(5-(4-chloro-3,5-dimethoxyphenyl) furan-2-yl)-2-ethoxy-2-(4-(5-methyl-1,3,4-thiadiazol-2-yl) phenyl)ethanone, is a PDE10 inhibitor.

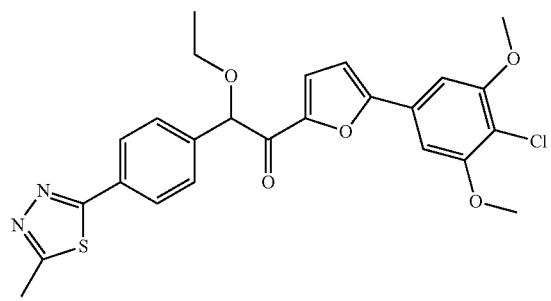

(I)

Compound (I) falls within the scope of PDE10 inhibitors disclosed in International PCT Application Publication No. WO 2011/112828. Compound (I) is specifically disclosed as compound no. 65-10 in International PCT Application No. WO 2011/112828. Compound (I) can be prepared according to the general procedures found in International PCT Application Publication No. WO 2011/112828, which are herein incorporated by reference.

In drug development, it is necessary to produce a compound that can enable a formulation to meet targeted pharmaceutical requirements and specifications. This may be achieved through the use of a stable crystalline form (sometimes referred to as a polymorph) of the drug. It is desirable to select a drug form that is easily and consistently manufactured, has good handling characteristics suitable for large-scale manufacturing and in formulating dosage forms so that it can be produced on a large-scale in a cost-efficient manner, is sufficiently shelf-stable such that does not change polymorphic form during manufacturing, shipment, or storage, and has suitable bioavailability and release characteristics. The present invention fulfills these needs and provides further related advantages.

BRIEF SUMMARY

This invention is directed to various novel crystalline forms of Compound (I) as described herein, methods for the preparation thereof, pharmaceutical compositions thereof, and their use as a PDE10 inhibitor.

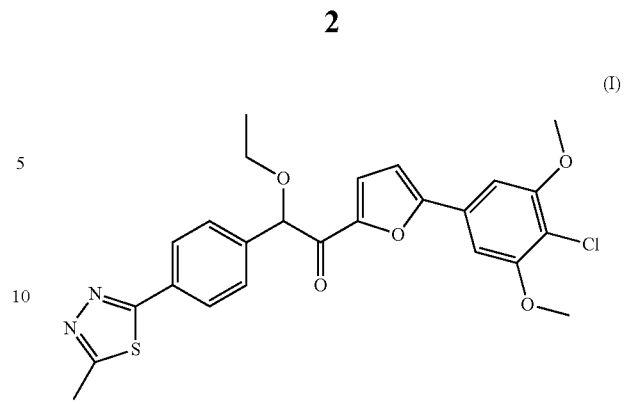

(I)

Further objects of this invention arise for one skilled in the art from the following description and the examples.

In one embodiment, the invention is directed to various polymorphic forms of Compound (I):

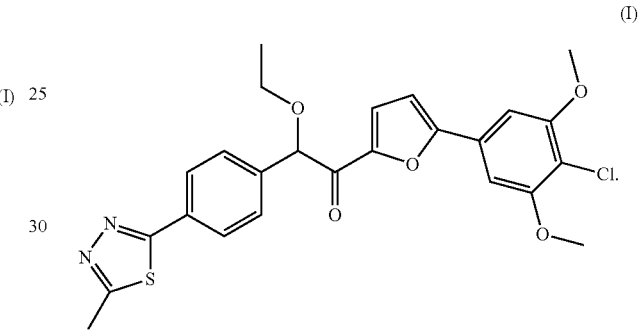

(I)

The various polymorphic forms of Compound (I) are characterized by unique XRPD spectra and are labeled as Form A, Form B, Form C, Form D, Form E, Form F, shifted Form F, and Form G. Polymorphic forms A, B, and D are characterized as anhydrous polymorphs of Compound (I). Polymorphic forms C and E are characterized as solvates of Compound (I). Polymorphic form F and shifted form F represent the same polymorph and is characterized as a variable hydrate of Compound (I). Polymorphic form G is characterized as a monohydrate of Compound (I).

Form F

A particularly suitable polymorphic form of Compound (I) is form F, which is a crystalline hydrate of Compound (I) which may contain a variable amount of water (which can be referred to as a crystalline variable hydrate of Compound (I)) which can include up to about a half mole of water per mole of Compound (I) at ambient conditions.

In a further embodiment of the invention, the variable hydrate of Compound (I) is crystalline Form F.

In a further embodiment of the invention, the crystalline variable hydrate of Compound (I), Form F, has a primitive monoclinic lattice Bravais type.

In a further embodiment of the invention, the crystalline variable hydrate of Compound (I), Form F, has a primitive monoclinic lattice comprising vectors wherein a is about 8.655 Å, α is about 90°, b is about 17.893 Å, β is about 102.67°, c is about 16.315 Å, and γ is about 90°.

In a further embodiment of the invention, the crystalline variable hydrate of Compound (I), Form F, has a space group of $P2_1/c$.

In a further embodiment of the invention, the crystalline variable hydrate of Compound (I), Form F, has an X-ray powder diffraction pattern comprising peaks at about 9.9, 12.2, and 14.9 degrees 2θ (e.g., ±0.2 degrees 2θ) when measured using CuKα radiation.

In a further embodiment of the invention, the crystalline variable hydrate of Compound (I), Form F, has an X-ray powder diffraction pattern further comprising peaks at about 9.9, 10.4, 12.2, 14.9, 19.5, 20.1, 22.5, 22.9, and 25.8 degrees 2θ (e.g., ±0.2 degrees 2θ) when measured using CuKα radiation.

In a further embodiment of the invention, the crystalline variable hydrate of Compound (I), Form F, has an X-ray powder diffraction pattern substantially the same as that shown in FIG. 24, measured under conditions as described herein.

In a further embodiment of the invention, the crystalline variable hydrate of Compound (I), Form F, has a DSC thermogram substantially the same as that shown in FIG. 5, measured under conditions as described herein.

In a further embodiment of the invention, the crystalline variable hydrate of Compound (I), Form F, has a TGA curve substantially the same as that shown in FIG. 6, measured under conditions as described herein.

In a further embodiment of the invention, the crystalline variable hydrate of Compound (I), Form F, has a dynamic vapor sorption isotherm substantially the same as that shown in FIG. 7, measured under conditions as described herein.

In a further embodiment of the invention, the crystalline variable hydrate of Compound (I), Form F, has an X-ray powder diffraction pattern comprising peaks at about 9.9, 12.2, and 14.9 degrees 2θ (e.g., ±0.2 degrees 2θ) when measured using CuKα radiation and a DSC thermogram substantially the same as that shown in FIG. 5.

In a further embodiment of the invention, the crystalline variable hydrate of Compound (I), Form F, has an X-ray powder diffraction pattern comprising peaks at about 9.9, 12.2, and 14.9 degrees 2θ (e.g., ±0.2 degrees 2θ) when measured using CuKα radiation and a TGA curve substantially the same as that shown in FIG. 6.

In a further embodiment of the invention, the crystalline variable hydrate of Compound (I), Form F, has an X-ray powder diffraction pattern comprising peaks at about 9.9, 12.2, and 14.9 degrees 2θ (e.g., ±0.2 degrees 2θ) when measured using CuKα radiation and a dynamic vapor sorption isotherm substantially the same as that shown in FIG. 7.

In still other embodiments of the invention, the crystalline variable hydrate of Compound (I), Form F, has any combination of two or more of the following: (a) an X-ray powder diffraction pattern comprising peaks at about 9.9, 12.2, and 14.9 degrees 2θ (e.g., ±0.2 degrees 2θ) when measured using CuKα radiation; (b) a DSC thermogram substantially the same as that shown in FIG. 5; (c) a TGA curve substantially the same as that shown in FIG. 6; and (d) a dynamic vapor sorption isotherm substantially the same as that shown in FIG. 7.

In a further embodiment of the invention, the crystalline variable hydrate of Compound (I), Shifted Form F, has an X-ray powder diffraction pattern substantially the same as that shown in FIG. 1, measured under conditions as described herein.

In a further embodiment of the invention, the crystalline variable hydrate of Compound (I), Shifted Form F, has a DSC thermogram substantially the same as that shown in FIG. 9, measured under conditions as described herein.

In a further embodiment of the invention, the crystalline variable hydrate of Compound (I), Shifted Form F, has a TGA curve substantially the same as that shown in FIG. 10, measured under conditions as described herein.

In a further embodiment of the invention, the crystalline variable hydrate of Compound (I), Shifted Form F, has a dynamic vapor sorption isotherm substantially the same as that shown in FIG. 11, measured under conditions as described herein.

Form A

One embodiment of a polymorphic form of Compound (I) is form A, which is an anhydrous crystalline form of Compound (I).

In a further embodiment of the invention, the anhydrous crystalline of Compound (I), Form A, has an X-ray powder diffraction pattern comprising peaks at about 5.6, 11.2, 16.0, and 21.4 degrees 2θ (e.g., ±0.2 degrees 2θ) when measured using CuKα radiation.

In a further embodiment of the invention, the anhydrous crystalline form of Compound (I), Form A, has an X-ray powder diffraction pattern further comprising peaks at about 5.6, 11.2, 16.0, 20.0, 21.4, 24.2, and 25.2 degrees 2θ (e.g., ±0.2 degrees 2θ) when measured using CuKα radiation.

In a further embodiment of the invention, the anhydrous crystalline form of Compound (I), Form A, has an X-ray powder diffraction pattern substantially the same as that shown in FIG. 25, measured under conditions as described herein.

In a further embodiment of the invention, the anhydrous crystalline of Compound (I), Form A, has a DSC thermogram substantially the same as that shown in FIG. 14, measured under conditions as described herein.

In a further embodiment of the invention the anhydrous crystalline of Compound (I), Form A, has a TGA curve substantially the same as that shown in FIG. 15, measured under conditions as described herein.

In a further embodiment of the invention, the anhydrous crystalline of Compound (I), Form A, has an X-ray powder diffraction pattern comprising peaks at about 5.6, 11.2, 16.0, and 21.4 degrees 2θ (e.g., ±0.2 degrees 2θ) when measured using CuKα radiation and a DSC thermogram substantially the same as that shown in FIG. 14.

In a further embodiment of the invention, the anhydrous crystalline of Compound (I), Form A, has an X-ray powder diffraction pattern comprising peaks at about 5.6, 11.2, 16.0, and 21.4 degrees 2θ (e.g., ±0.2 degrees 2θ) when measured using CuKα radiation and a TGA curve substantially the same as that shown in FIG. 15.

In still other embodiments of the invention, the anhydrous crystalline of Compound (I), Form A, has any combination of two or more of the following: (a) an X-ray powder diffraction pattern comprising peaks at about 5.6, 11.2, 16.0, and 21.4 degrees 2θ (e.g., ±0.2 degrees 2θ) when measured using CuKα radiation; (b) a DSC thermogram substantially the same as that shown in FIG. 14; and (c) a TGA curve substantially the same as that shown in FIG. 15.

Form B

One embodiment of a polymorphic form of Compound (I) is Form B, which is an anhydrous crystalline form of Compound (I).

In a further embodiment of the invention, the anhydrous crystalline form of Compound (I), Form B, has an X-ray powder diffraction pattern comprising peaks at about 12.7, 18.6, and 20.0 degrees 2θ (e.g., ±0.2 degrees 2θ) when measured using CuKα radiation.

In a further embodiment of the invention, the anhydrous crystalline form of Compound (I), Form B, has an X-ray powder diffraction pattern further comprising peaks at about 12.7, 18.6, 20.0, 21.7, 23.1, and 25.6 degrees 2θ (e.g., ±0.2 degrees 2θ) when measured using CuKα radiation.

In a further embodiment of the invention, the anhydrous crystalline form of Compound (I), Form B, has an X-ray powder diffraction pattern substantially the same as that shown in FIG. 26, measured under conditions as described herein.

In a further embodiment of the invention, the anhydrous crystalline of Compound (I), Form B, has a DSC thermogram substantially the same as that shown in FIG. 17, measured under conditions as described herein.

In a further embodiment of the invention the anhydrous crystalline of Compound (I), Form B, has a TGA curve substantially the same as that shown in FIG. 18, measured under conditions as described herein.

In a further embodiment of the invention, the anhydrous crystalline of Compound (I), Form B, has an X-ray powder diffraction pattern comprising peaks at about 12.7, 18.6, and 20.0 degrees 2θ (e.g., ±0.2 degrees 2θ) when measured using CuKα radiation and a DSC thermogram substantially the same as that shown in FIG. 17.

In a further embodiment of the invention, the anhydrous crystalline of Compound (I), Form B, has an X-ray powder diffraction pattern comprising peaks at about 12.7, 18.6, and 20.0 degrees 2θ (e.g., ±0.2 degrees 2θ) when measured using CuKα radiation and a TGA curve substantially the same as that shown in FIG. 18.

In still other embodiments of the invention, the anhydrous crystalline of Compound (I), Form B, has any combination of two or more of the following: (a) an X-ray powder diffraction pattern comprising peaks at about 12.7, 18.6, and 20.0 degrees 2θ (e.g., ±0.2 degrees 2θ) when measured using CuKα radiation; (b) a DSC thermogram substantially the same as that shown in FIG. 17; and (c) a TGA curve substantially the same as that shown in FIG. 18.

Form C

One embodiment of a polymorphic form of Compound (I) is Form C, which is an IPAc solvate of Compound (I).

In a further embodiment of the invention, the IPAc solvate of Compound (I), Form C, has an X-ray powder diffraction pattern comprising peaks at about 11.4, 18.8, 21.2, and 22.7 degrees 2θ (e.g., ±0.2 degrees 2θ) when measured using CuKα radiation.

In a further embodiment of the invention, the IPAc solvate of Compound (I), Form C, has an X-ray powder diffraction pattern further comprising peaks at about 10.2, 11.4, 12.3, 16.1, 16.8, 18.8, 20.3, 21.2, and 22.7 degrees 2θ (e.g., ±0.2 degrees 2θ) when measured using CuKα radiation.

In a further embodiment of the invention, the IPAc solvate of Compound (I), Form C, has an X-ray powder diffraction pattern substantially the same as that shown in FIG. 27, measured under conditions as described herein.

In a further embodiment of the invention, the IPAc solvate of Compound (I), Form C, has a DSC thermogram substantially the same as that shown in FIG. 20, measured under conditions as described herein.

In a further embodiment of the invention, the IPAc solvate of Compound (I), Form C, has an X-ray powder diffraction pattern comprising peaks at about 11.4, 18.8, 21.2, and 22.7 degrees 2θ (e.g., ±0.2 degrees 2θ) when measured using CuKα radiation and a DSC thermogram substantially the same as that shown in FIG. 20.

Form D

One embodiment of a polymorphic form of Compound (I) is form D, which is an anhydrous crystalline form of Compound (I).

In a further embodiment of the invention, the anhydrous crystalline of Compound (I), Form D has an X-ray powder diffraction pattern comprising peaks at about 15.9, 21.4, and 24.2 degrees 2θ (e.g., ±0.2 degrees 2θ) when measured using CuKα radiation.

In a further embodiment of the invention, the anhydrous crystalline of Compound (I), Form D, has an X-ray powder diffraction pattern substantially the same as that shown in FIG. 28, measured under conditions as described herein.

In a further embodiment of the invention, the anhydrous crystalline of Compound (I), Form D, has a DSC thermogram substantially the same as that shown in FIG. 22, measured under conditions as described herein.

In a further embodiment of the invention the anhydrous crystalline of Compound (I), Form D, has a TGA curve substantially the same as that shown in FIG. 23, measured under conditions as described herein.

In a further embodiment of the invention, the anhydrous crystalline of Compound (I), Form D, has an X-ray powder diffraction pattern comprising peaks at about 15.9, 21.4, and 24.2 degrees 2θ (e.g., ±0.2 degrees 2θ) when measured using CuKα radiation and a DSC thermogram substantially the same as that shown in FIG. 22.

In a further embodiment of the invention, the anhydrous crystalline of Compound (I), Form D, has an X-ray powder diffraction pattern comprising peaks at about 15.9, 21.4, and 24.2 degrees 2θ (e.g., ±0.2 degrees 2θ) when measured using CuKα radiation and a TGA curve substantially the same as that shown in FIG. 23.

In still other embodiments of the invention, the anhydrous crystalline of Compound (I), Form D, has any combination of two or more of the following: (a) an X-ray powder diffraction pattern comprising peaks at about 15.9, 21.4, and 24.2 degrees 2θ (e.g., ±0.2 degrees 2θ) when measured using CuKα radiation; (b) a DSC thermogram substantially the same as that shown in FIG. 22; and (c) a TGA curve substantially the same as that shown in FIG. 23.

Form E

One embodiment of a polymorphic form of Compound (I) is Form E, which is a THF solvate of Compound (I).

In a further embodiment of the invention, the THF solvate of Compound (I), Form E, has an X-ray powder diffraction pattern comprising peaks at about 8.0, 12.5, 16.2, and 18.4 degrees 2θ (e.g., ±0.2 degrees 2θ) when measured using CuKα radiation.

In a further embodiment of the invention, the THF solvate of Compound (I), Form E, has an X-ray powder diffraction pattern further comprising peaks at about 8.0, 12.5, 15.9, 16.2, 18.4, 22.9, and 28.5 degrees 2θ (e.g., ±0.2 degrees 2θ) when measured using CuKα radiation.

In a further embodiment of the invention, the THF solvate of Compound (I), Form E, has an X-ray powder diffraction pattern substantially the same as that shown in FIG. 29, measured under conditions as described herein.

Another embodiment of the invention is a pharmaceutical composition comprising a polymorph of Compound (I) and at least one pharmaceutically acceptable carrier or diluent. In further embodiments, the polymorph of Compound (I) is Form A, Form B, Form C, Form D, Form E, Form F, shifted Form F, or Form G. In a particular embodiment, the pharmaceutical composition comprises a polymorph of Form F, having an XPRD pattern of Form F or shifted Form F.

Another embodiment of the invention is a method for inhibiting PDE10 in a warm-blooded animal, comprising administering to the animal an effective amount of a crystalline variable hydrate of Compound (I), for example Form F or shifted Form F, or pharmaceutical composition thereof.

Another embodiment of the invention is a method for treating a neurological disorder in a warm-blooded animal having said neurological disorder, comprising administering to the animal an effective amount of a crystalline variable hydrate of Compound (I), for example Form F or shifted Form F, or a pharmaceutically composition thereof, wherein the neurological disorder is selected from the group consisting of psychotic disorders, anxiety disorders, Parkinson's disease, Huntington's disease, Alzheimer's disease, encephalitis, phobias, epilepsy, aphasia, Bell's palsy, cerebral palsy, sleep disorders, pain, Tourette's syndrome, schizophrenia, delusional disorders, bipolar disorders, post-traumatic stress disorders, drug-induced psychosis, panic disorders, obsessive-compulsive disorders, attention-deficit disorders, disruptive behavior disorders, autism, depression, dementia, epilepsy, insomnias and multiple sclerosis.

In a further embodiment of the invention, the neurological disorder is schizophrenia.

In a further embodiment of the invention, the neurological disorder is post-traumatic stress disorder.

Another embodiment of the invention is a process to prepare a polymorph of Compound (I), for example a crystalline Form F of the variable hydrate of Compound (I), wherein said process is selected from the group consisting of cooling, crash precipitation, drying, evaporation, wet grinding, melt/cool, RH stress, slurry, vapor diffusion, and vapor stress.

DETAILED DESCRIPTION

Definitions

Figure 1:
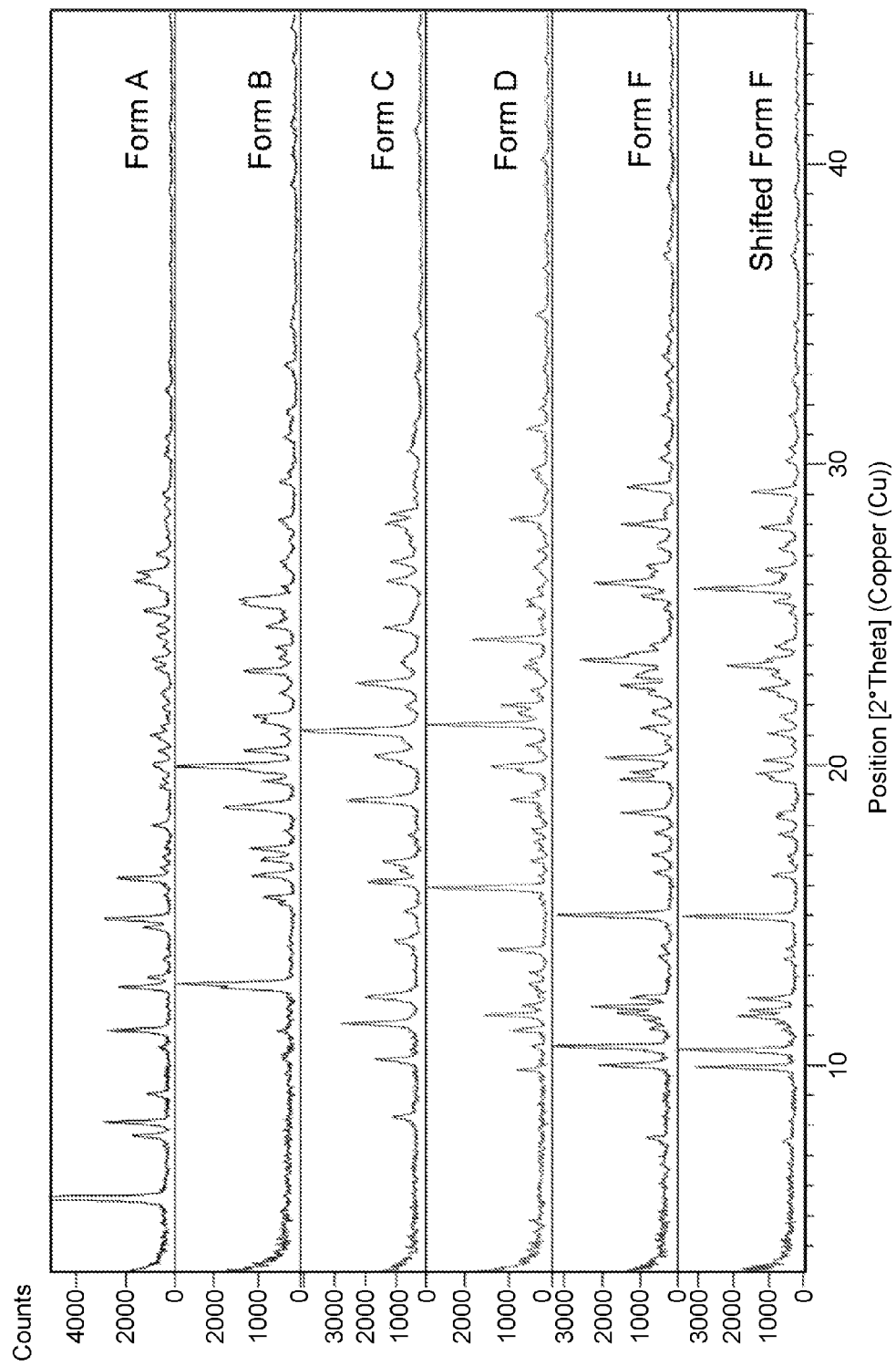
FIG. 1 shows X-ray powder diffraction (XRPD) patterns of the polymorphic Forms A, B, C, D, F, and shifted F of Compound (I) as disclosed herein.
Figure 2:
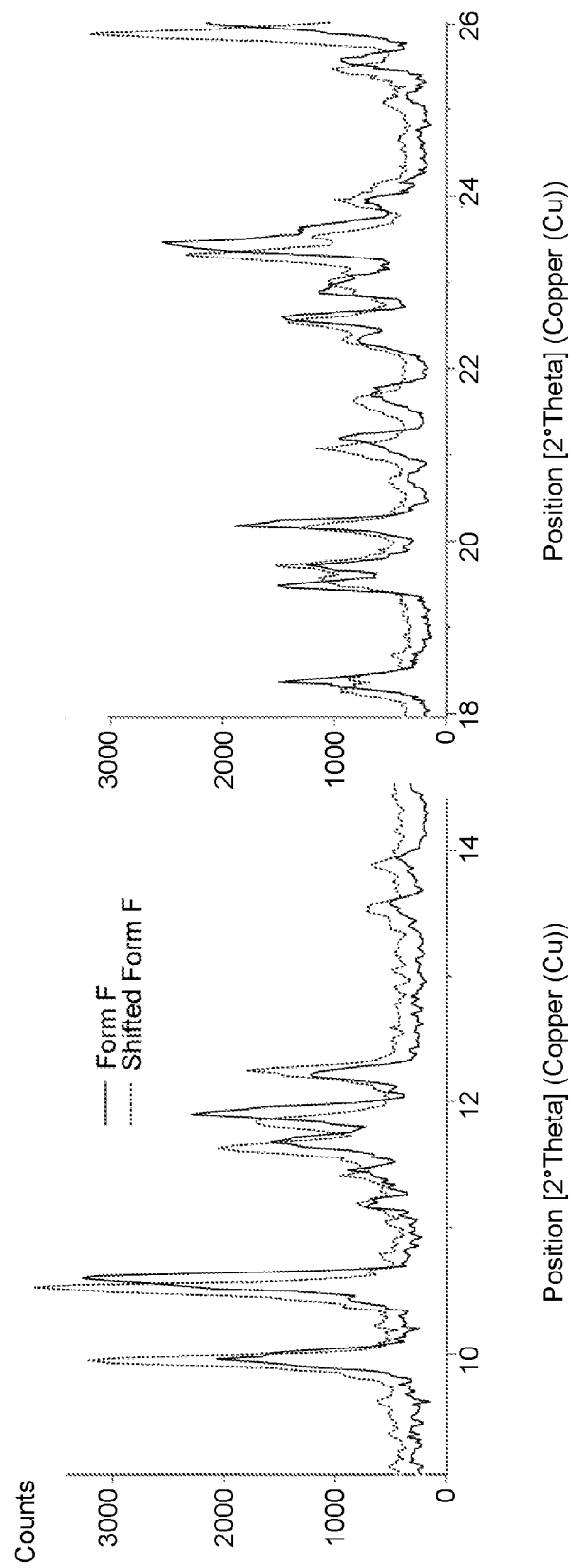
FIG. 2 shows shifting of XRPD peaks between Form F and shifted F of Compound (I).

Terms not specifically defined herein should be given the meanings that would be given to them by one of skill in the art in light of the disclosure and the context. As used throughout the present application, however, unless specified to the contrary, the following terms have the meaning indicated:

The term "solvate" refers to a crystalline solid containing amounts of a solvent incorporated within the crystal structure. As used herein, the term "solvate" includes hydrates if the incorporated solvent is water.

The term "non-solvate" refers to a crystalline solid in which no solvent molecules occupy a specific crystallographic site.

The term "pharmaceutically acceptable" with respect to a substance as used herein means that substance which is, within the scope of sound medical judgment, suitable for use in contact with the tissues of humans and lower animals without undue toxicity, irritation, allergic response, and the like, commensurate with a reasonable benefit/risk ratio, and effective for the intended use when the substance is used in a pharmaceutical composition.

The term "treating" with respect to the treatment of a disease-state in a patient includes (i) inhibiting or ameliorating the disease-state in a patient, e.g., arresting or slowing its development; or (ii) relieving the disease-state in a patient, i.e., causing regression or cure of the disease-state.

The term "Bravais lattice type" refers to the characterization of the crystal lattice structure. A crystal is made up of a periodic arrangement of one or more atoms repeated at each lattice point. There are 14 conventional Bravais lattices describing varying unit cell configurations of a crystal structure, including a primitive monoclinic system. A primitive lattice centering has lattice points on the cell corners only. A monoclinic lattice system is described by three vectors. In the monoclinic system, the crystal is described by vectors of unequal length. Two of the vectors are perpendicular and the third makes an angle other than 90°. They form a rectangular prism with a parallelogram as the base.

Variable Hydrate of Compound (I)

Variable hydrates are crystalline materials with differing quantities of water in the unit cell depending upon the temperature and ambient water activity. Hydrates of Compound (I) can be isolated in a crystalline form. The non-crystalline or crystalline forms may exist as a solvate or non-solvate.

Crystalline Form F

Crystalline samples displaying the Form F XRPD spectral pattern or spectra may show minor shifts in the spectral pattern suggestive of the ability of the crystal lattice to expand or contract to accommodate additional water. The XRPD pattern with some shifted peaks is referred to as "Shifted Form F". Form F and shifted F are interchangeable depending on humidity environment and drying conditions.

The characterization data of Form F and shifted Form F suggests that water content in the material is humidity dependent. Samples tend to have low water content in winter when ambient humidity is in the vicinity of 20% RH and water content of the material is higher when ambient humidity increases to around 50-60% RH. Characterization results showed that Form F and shifted F are the same polymorph. Characterization of Form F and Shifted Form F material has shown that both patterns are easily interchangeable and readily convert to one or the other based on ambient humidity.

Figure 3:
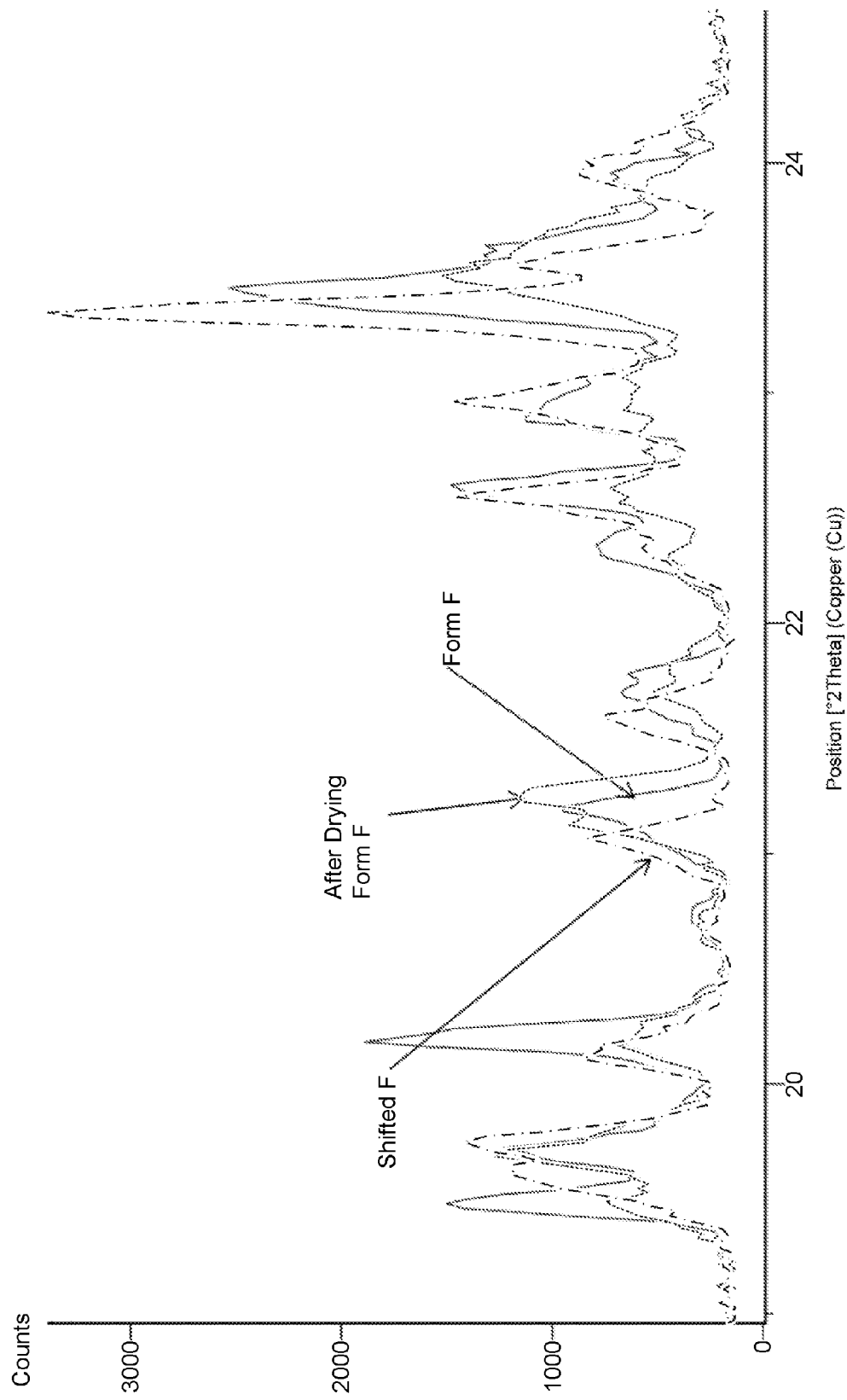
FIG. 3 shows XRPD interconversion between Form F and shifted Form F upon drying. (Only a part of the XRPD pattern is highlighted.)
Figure 4:
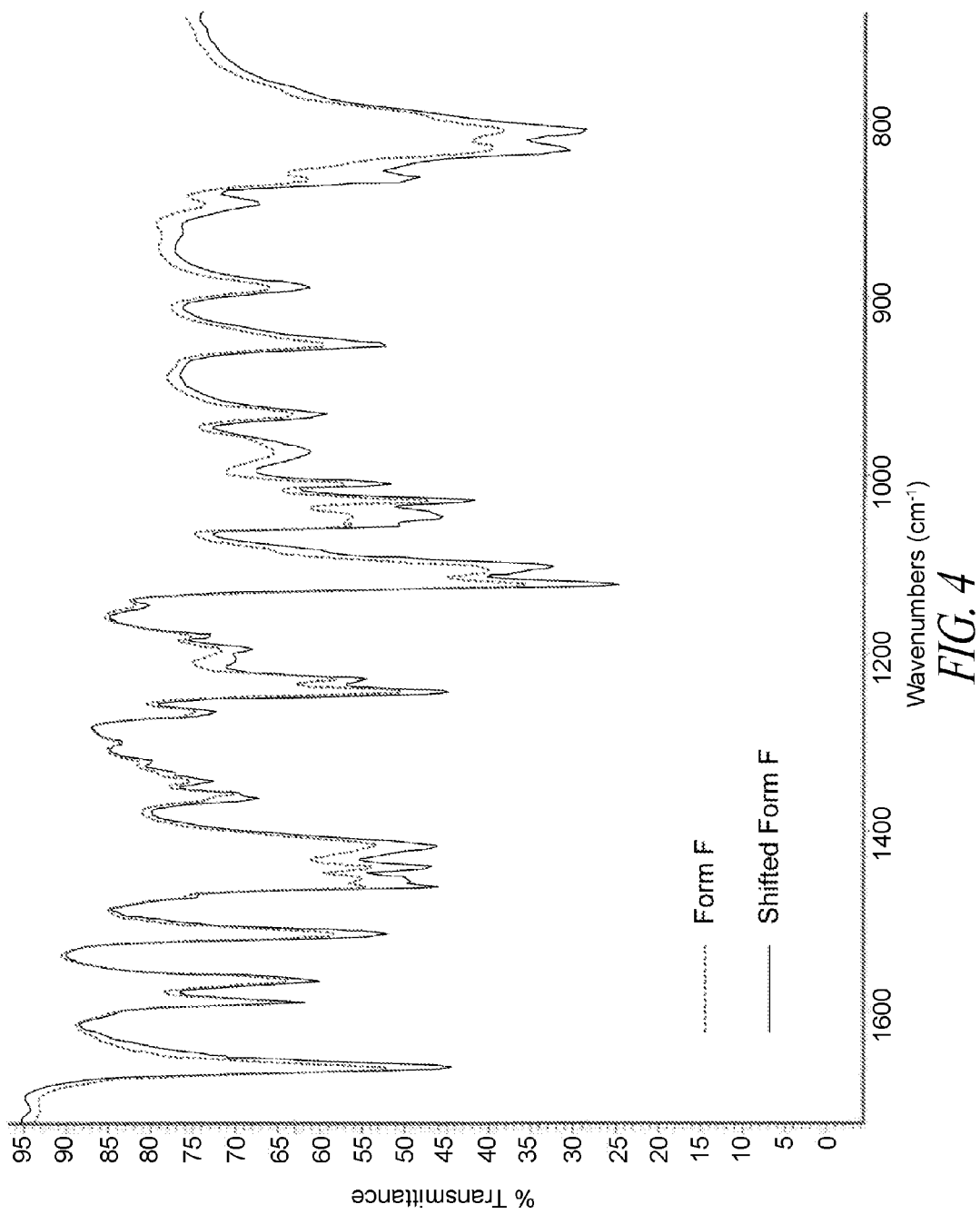
FIG. 4 is an IR spectra of Form F and shifted Form F.

To understand a change of Form F to shifted Form F, a drying study was conducted wherein a variable hydrate having shifted Form F was dried overnight under vacuum at 50° C. XRPD of the dried solid was consistent with Form F. The dried Form F material was exposed to ambient conditions for 5 days by allowing it to sit on the XRPD slide in the hood. The material reabsorbed moisture and converted back to shifted Form F. The conversion from shifted Form F to Form F is depicted in the FIG. 3. This study confirms that Form F absorbs moisture from the atmosphere and depending upon the relative humidity of the environment either remains Form F or converts to Shifted Form F.

When water content in the Form F is high the XRPD pattern shifts toward the left and this form is referred to as shifted Form F. When the sample is heated to 50° C. during drying the material dehydrates, and the XRPD pattern shifts to the right and this pattern is referred to Form F. Depending upon the ambient humidity the sample picks up moisture and Form F converts to shifted Form F. Apart from the shifting of a few peaks the two patterns are essentially identical which indicates that Form F and shifted Form F are the same and the level of water dictates the minor shifting of select peaks.

Figure 24:
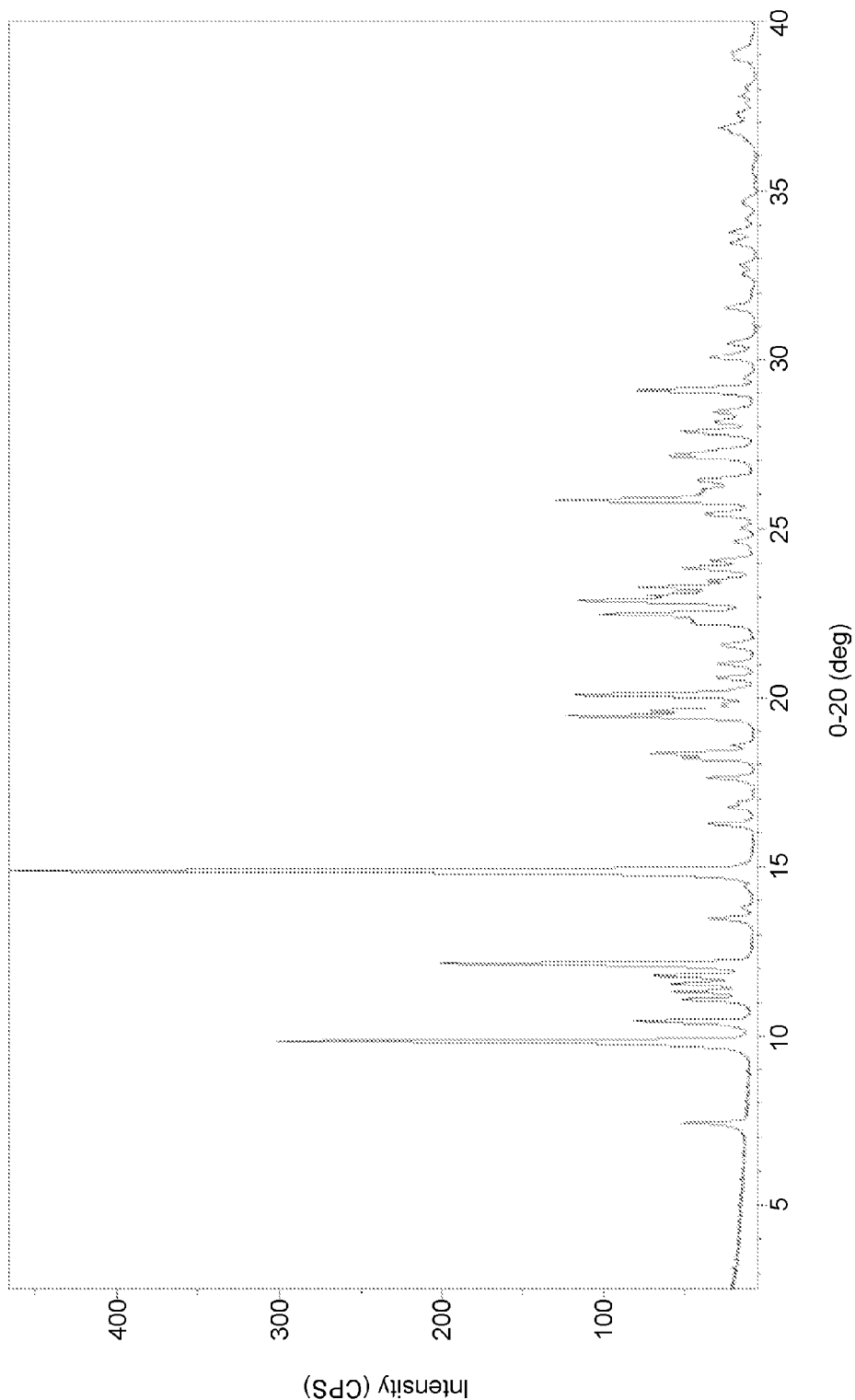
FIG. 24 is the X-ray powder diffraction (XRPD) pattern of the variable hydrate of Compound (I), Form F.
Figure 25:
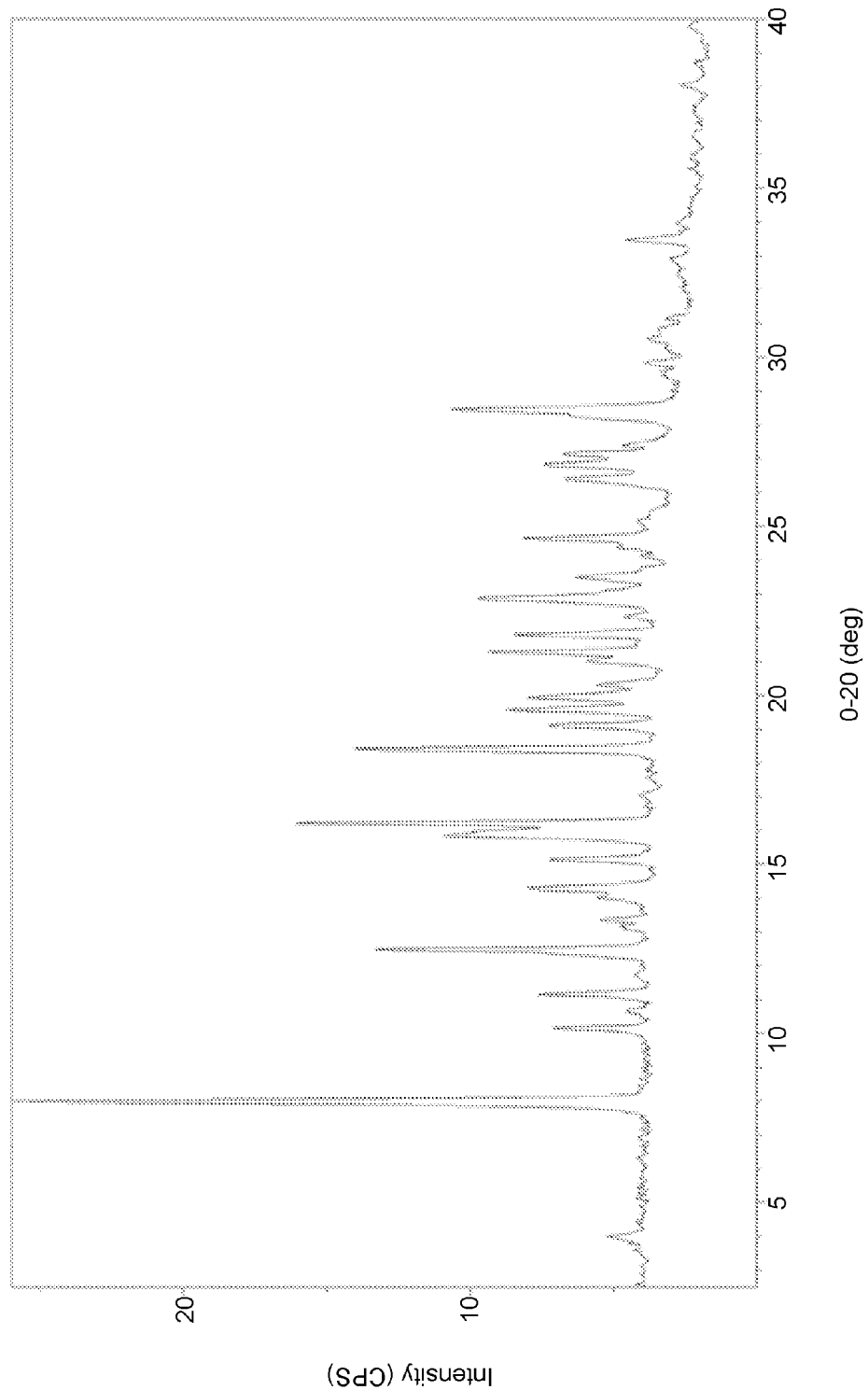
FIG. 25 is the X-ray powder diffraction (XRPD) pattern of the polymorphic Form A of compound (I).
Figure 26:
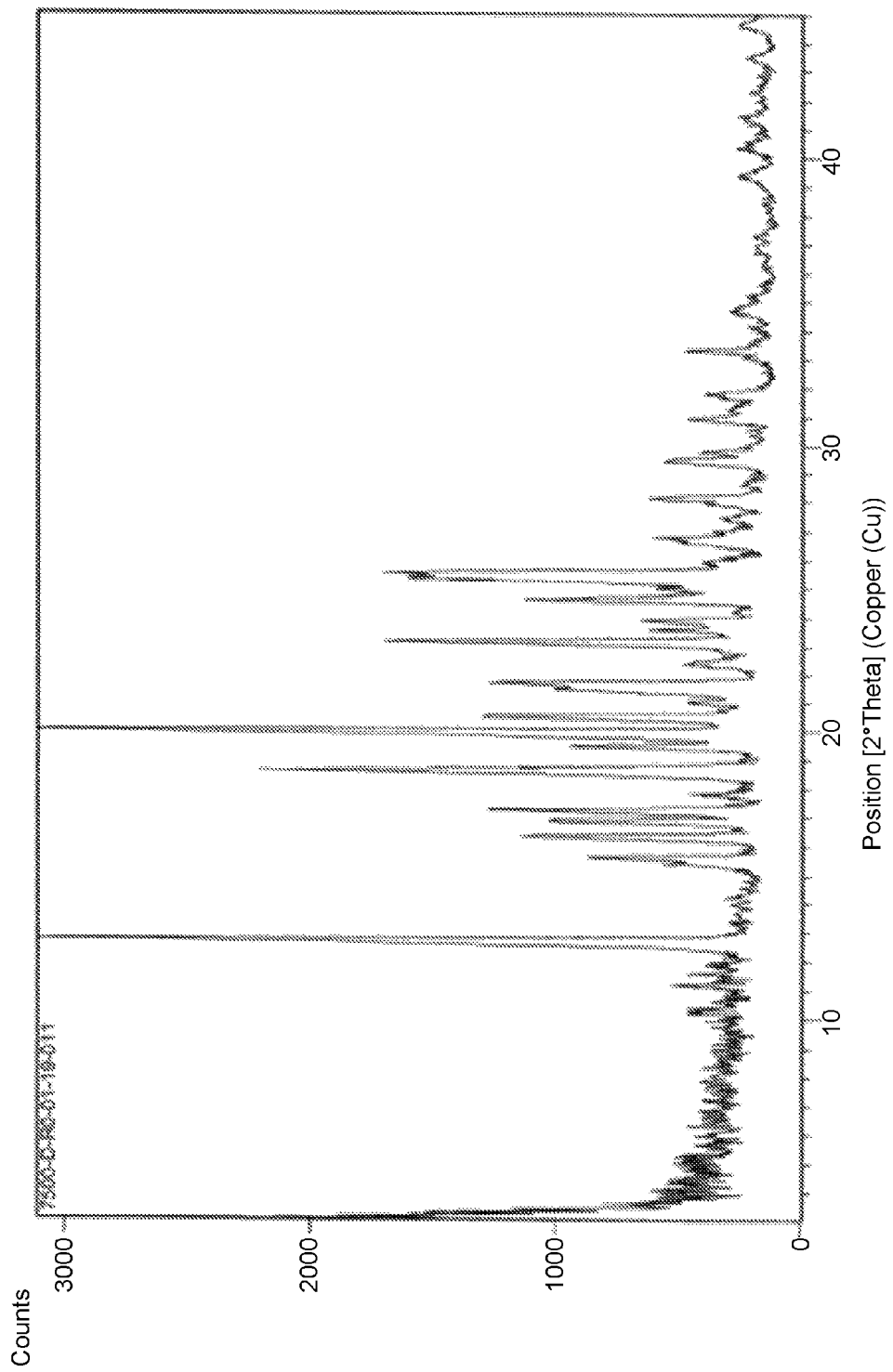
FIG. 26 is the X-ray powder diffraction (XRPD) pattern of the polymorphic Form B of compound (I).
Figure 27:
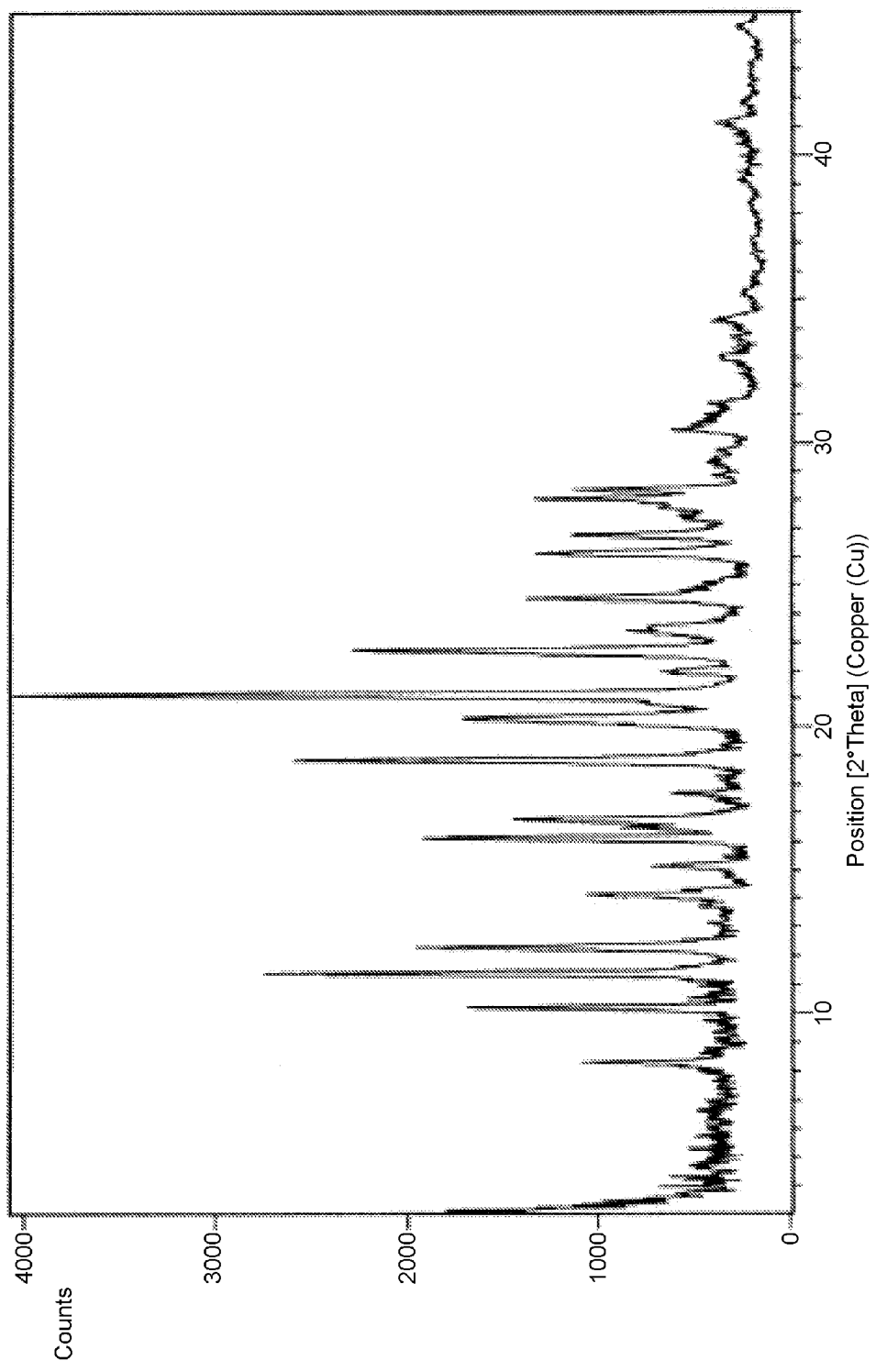
FIG. 27 is the X-ray powder diffraction (XRPD) pattern of the polymorphic Form C of compound (I).
Figure 28:
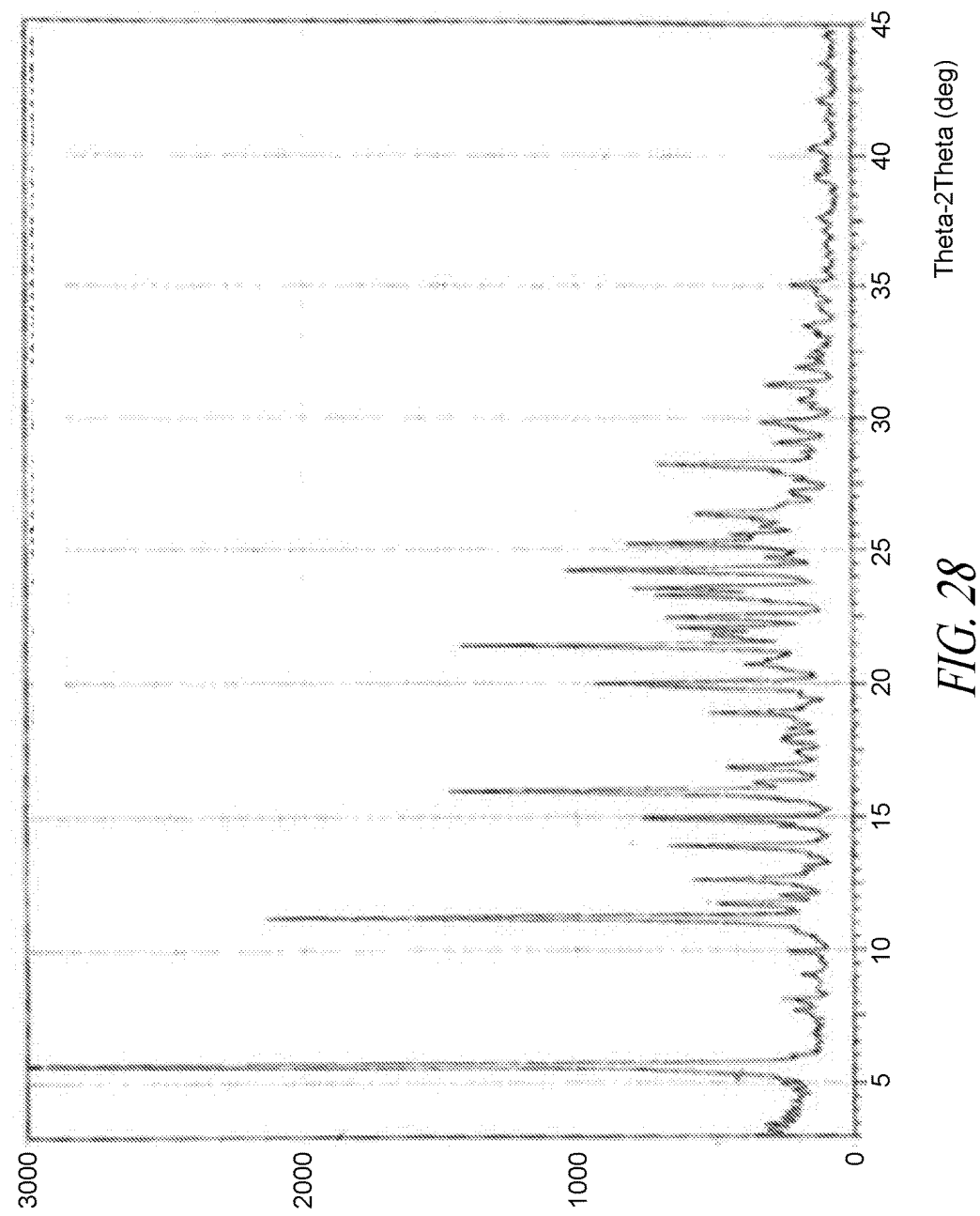
FIG. 28 is the X-ray powder diffraction (XRPD) pattern of the polymorphic Form D of compound (I).

The XRPD pattern of variable hydrate of Compound (I), Form F, is shown in FIG. 24. A list of peak positions and relative intensities for the XRPD pattern in certain characteristic peak positions and relative intensities for the XRPD pattern in FIG. 24 for the variable hydrate of Compound (I), Form F, are shown in the following Table 1.

TABLE 1

| XPRD Peaks of Form F Form F of Compound (I) | |
|---|---|
| Angle 2-Theta ° | Relative Intensity % |
| 7.4 ± 0.2 | 11 |
| 9.9 ± 0.2 | 72 |

TABLE 1-continued

| XPRD Peaks of Form F Form F of Compound (I) | |
|---|---|
| Angle 2-Theta ° | Relative Intensity % |
| 10.4 ± 0.2 | 22 |
| 11.1 ± 0.2 | 12 |
| 11.3 ± 0.2 | 13 |
| 11.6 ± 0.2 | 14 |
| 11.8 ± 0.2 | 16 |
| 12.2 ± 0.2 | 42 |
| 13.5 ± 0.2 | 7 |
| 13.8 ± 0.2 | 4 |
| 14.4 ± 0.2 | 3 |
| 14.9 ± 0.2 | 100 |
| 16.3 ± 0.2 | 9 |
| 16.7 ± 0.2 | 5 |
| 16.9 ± 0.2 | 4 |
| 17.6 ± 0.2 | 8 |
| 18.2 ± 0.2 | 11 |
| 18.3 ± 0.2 | 14 |
| 18.6 ± 0.2 | 5 |
| 19.5 ± 0.2 | 26 |
| 19.6 ± 0.2 | 15 |
| 19.8 ± 0.2 | 6 |
| 20.1 ± 0.2 | 24 |
| 20.6 ± 0.2 | 7 |
| 21.0 ± 0.2 | 7 |
| 21.6 ± 0.2 | 6 |
| 22.2 ± 0.2 | 9 |
| 22.5 ± 0.2 | 21 |
| 22.9 ± 0.2 | 24 |
| 23.3 ± 0.2 | 18 |
| 23.5 ± 0.2 | 8 |
| 23.9 ± 0.2 | 11 |
| 24.1 ± 0.2 | 7 |
| 24.6 ± 0.2 | 4 |
| 25.0 ± 0.2 | 4 |
| 25.4 ± 0.2 | 9 |
| 25.8 ± 0.2 | 29 |
| 26.0 ± 0.2 | 9 |
| 26.2 ± 0.2 | 8 |
| 26.4 ± 0.2 | 10 |
| 27.1 ± 0.2 | 14 |
| 27.3 ± 0.2 | 8 |
| 27.8 ± 0.2 | 13 |
| 28.1 ± 0.2 | 8 |
| 28.4 ± 0.2 | 6 |
| 28.5 ± 0.2 | 6 |
| 29.1 ± 0.2 | 18 |
| 29.4 ± 0.2 | 3 |
| 30.1 ± 0.2 | 8 |
| 30.5 ± 0.2 | 6 |

In one embodiment, the invention is directed to a hydrate of Compound (I):

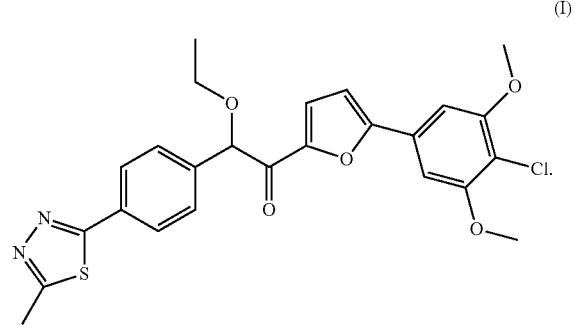 [SMILES: CCOC(C(=O)c1ccc(-c2cc(OC)c(Cl)c(OC)c2)o1)c1ccc(-c2nnc(C)s2)cc1]

(I)

The hydrate of Compound (I) may be in a non-crystalline or crystalline state, or a mixture of crystalline and non-crystalline forms.

In a further embodiment, the hydrate of Compound (I) may be a variable hydrate.

In a further embodiment of the invention, the hydrate of Compound (I) has crystalline Form F.

In a further embodiment of the invention, the crystalline hydrate of Compound (I) has a primitive monoclinic lattice Bravais type.

In a further embodiment of the invention, the crystalline hydrate of Compound (I) has a primitive monoclinic lattice comprising vectors wherein a is 8.655 Å, α is 90°, b is 17.893 Å, β is 102.67°, c is 16.315 Å, and γ is 90°.

In a further embodiment of the invention, the crystalline variable hydrate of Compound (I) has a space group of $P2_1/c$.

In a further embodiment of the invention, the crystalline variable hydrate of Compound (I) has an X-ray powder diffraction pattern comprising peaks at about 9.9, 12.2, and 14.9 degrees 2θ (e.g., ±0.2 degrees 2θ) when measured using CuKα radiation.

In a further embodiment of the invention, the crystalline variable hydrate of Compound (I) has an X-ray powder diffraction pattern further comprising peaks at about 9.9, 10.4, 12.2, 14.9, 19.5, 20.1, 22.5, 22.9, and 25.8 degrees 2θ (e.g., ±0.2 degrees 2θ) when measured using CuKα radiation.

In a further embodiment of the invention, the crystalline variable hydrate of Compound (I) has an X-ray powder diffraction pattern substantially the same as that shown in FIG. 24.

Figure 5:
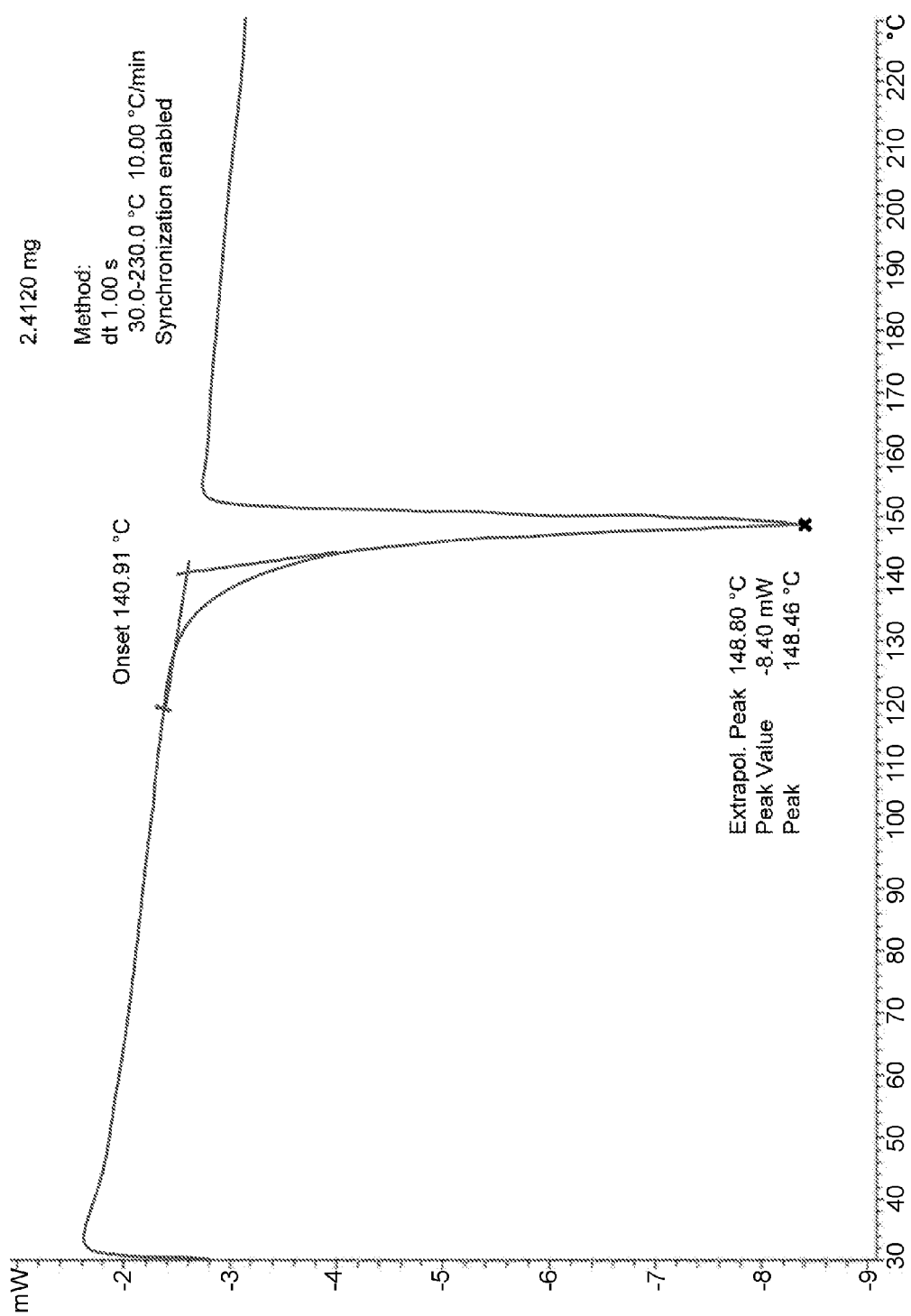
FIG. 5 is a DSC thermogram of the polymorphic Form F of compound (I).

In a further embodiment of the invention, the crystalline variable hydrate of Compound (I) has a DSC thermogram substantially the same as that shown in FIG. 5.

Figure 6:
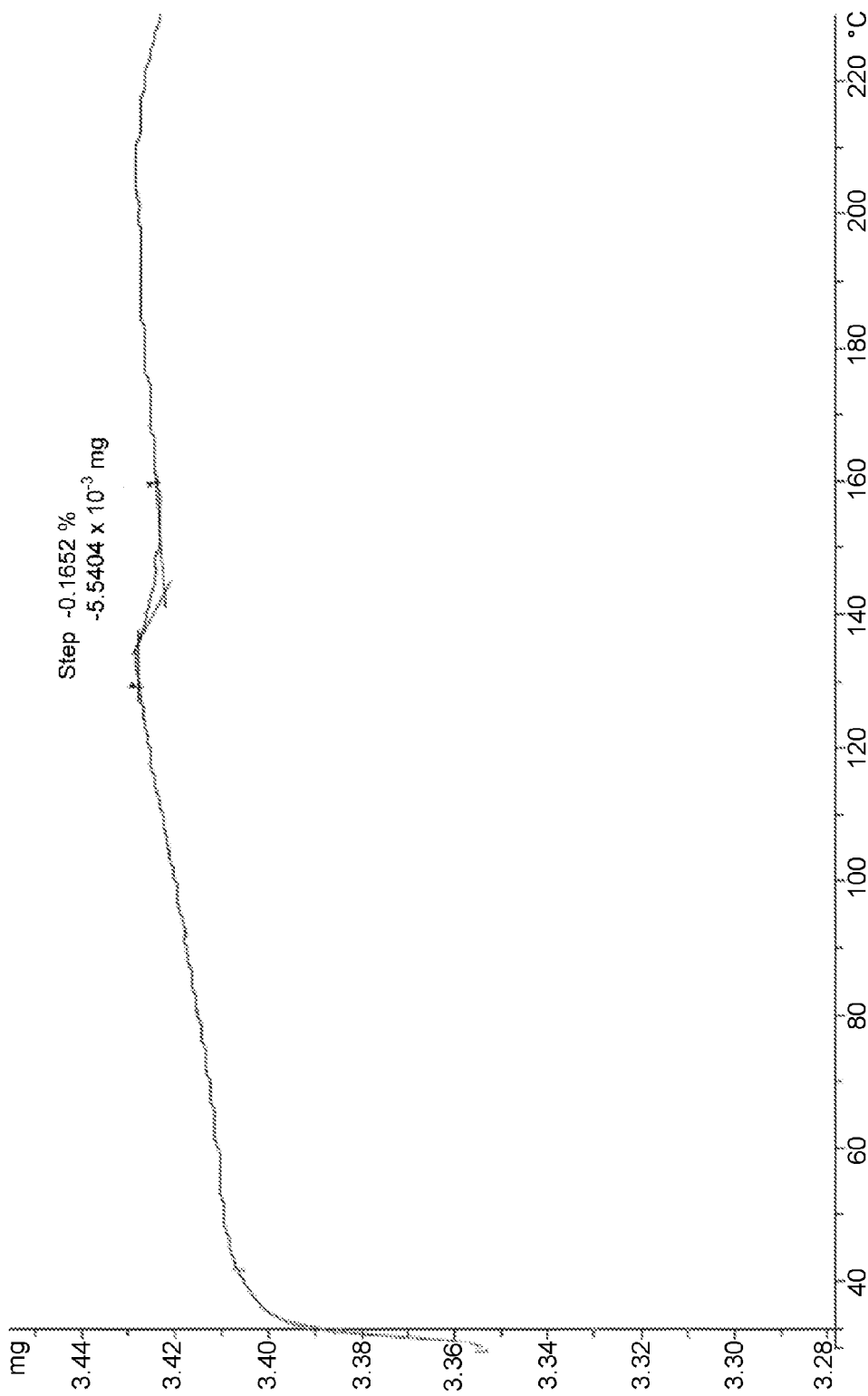
FIG. 6 is a TGA thermogram of the polymorphic Form F of compound (I).

In a further embodiment of the invention, the crystalline variable hydrate of Compound (I) has a TGA curve substantially the same as that shown in FIG. 6.

Figure 7:
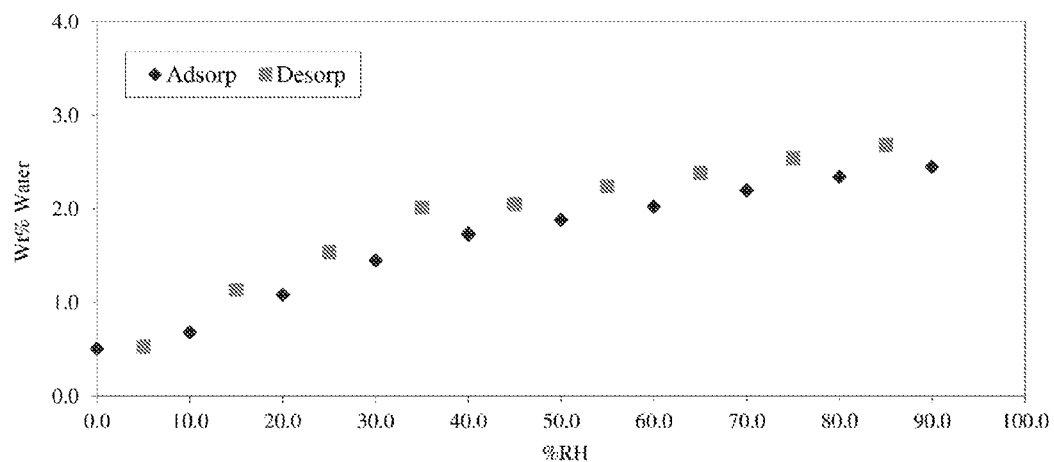
FIG. 7 is a gravimetric moisture sorption analysis of the polymorphic Form F of compound (I).

In a further embodiment of the invention, the crystalline variable hydrate of Compound (I) has a dynamic vapor sorption isotherm substantially the same as that shown in FIG. 7.

In a further embodiment of the invention, the crystalline variable hydrate of Compound (I) has an X-ray powder diffraction pattern comprising peaks at about 9.9, 12.2, and 14.9 degrees 2θ (e.g., ±0.2 degrees 2θ) when measured using CuKα radiation and a DSC thermogram substantially the same as that shown in FIG. 5.

In a further embodiment of the invention, the crystalline variable hydrate of Compound (I) has an X-ray powder diffraction pattern comprising peaks at about 9.9, 12.2, and 14.9 degrees 2θ (e.g., ±0.2 degrees 2θ) when measured using CuKα radiation and a TGA curve substantially the same as that shown in FIG. 6.

In a further embodiment of the invention, the crystalline hydrate of Compound (I) has an X-ray powder diffraction pattern comprising peaks at about 9.9, 12.2, and 14.9 degrees 2θ (e.g., ±0.2 degrees 2θ) when measured using CuKα radiation and a dynamic vapor sorption isotherm substantially the same as that shown in FIG. 7.

In still other embodiments of the invention, the crystalline variable hydrate of Compound (I) has any combination of two or more of the following: (a) an X-ray powder diffraction pattern comprising peaks at about 9.9, 12.2, and 14.9 degrees 2θ (e.g., ±0.2 degrees 2θ) when measured using CuKα radiation; (b) a DSC thermogram substantially the same as that shown in FIG. 5; (c) a TGA curve substantially the same as that shown in FIG. 6; and (d) a dynamic vapor sorption isotherm substantially the same as that shown in FIG. 7.

In a further embodiment of the invention, the crystalline variable hydrate of Compound (I), Shifted Form F, has an X-ray powder diffraction pattern substantially the same as that shown in FIG. 1, measured under conditions as described herein.

Figure 9:
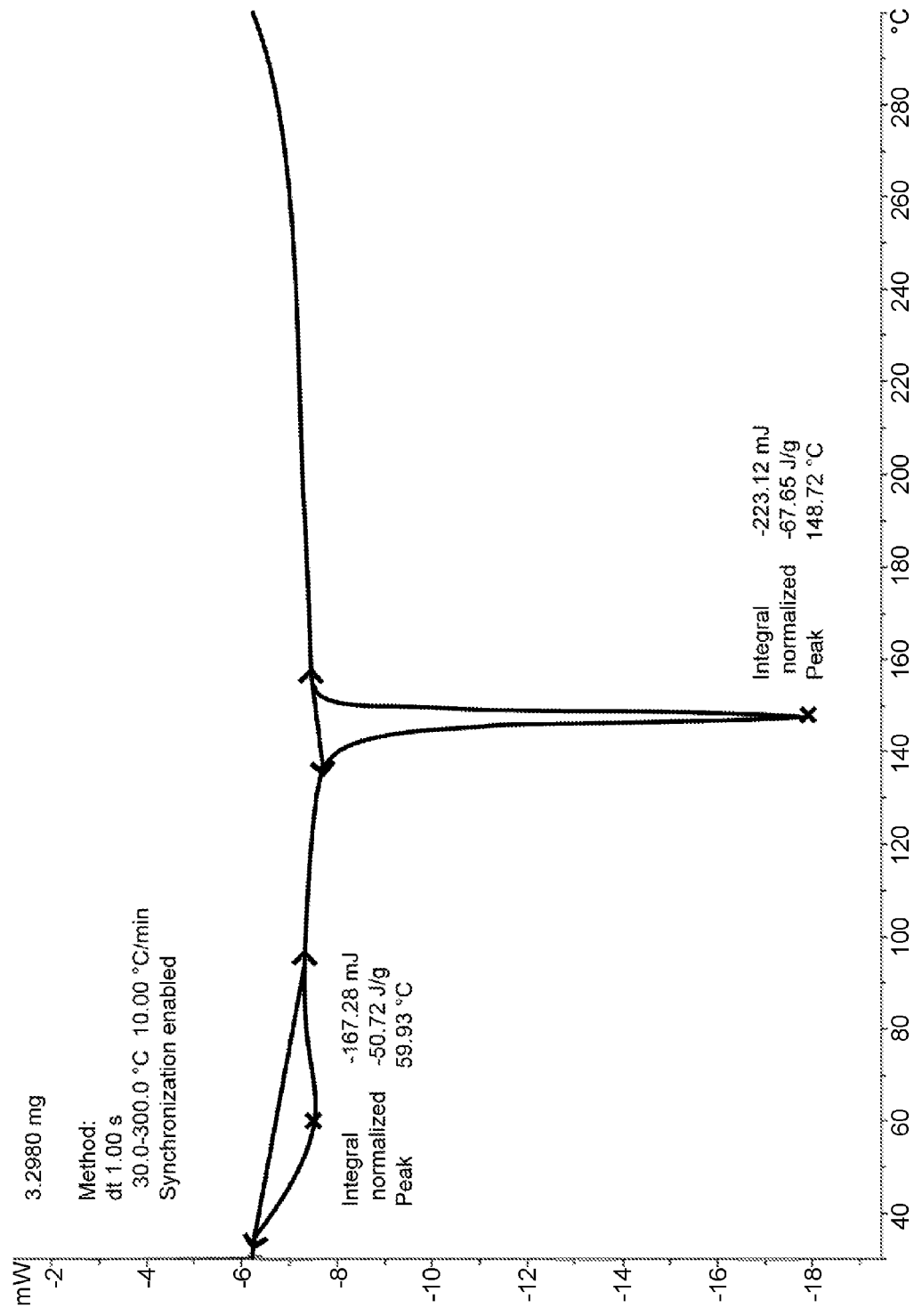
FIG. 9 is a DSC thermogram of the polymorphic Shifted Form F of compound (I).

In a further embodiment of the invention, the crystalline variable hydrate of Compound (I), Shifted Form F, has a DSC thermogram substantially the same as that shown in FIG. 9, measured under conditions as described herein.

Figure 10:
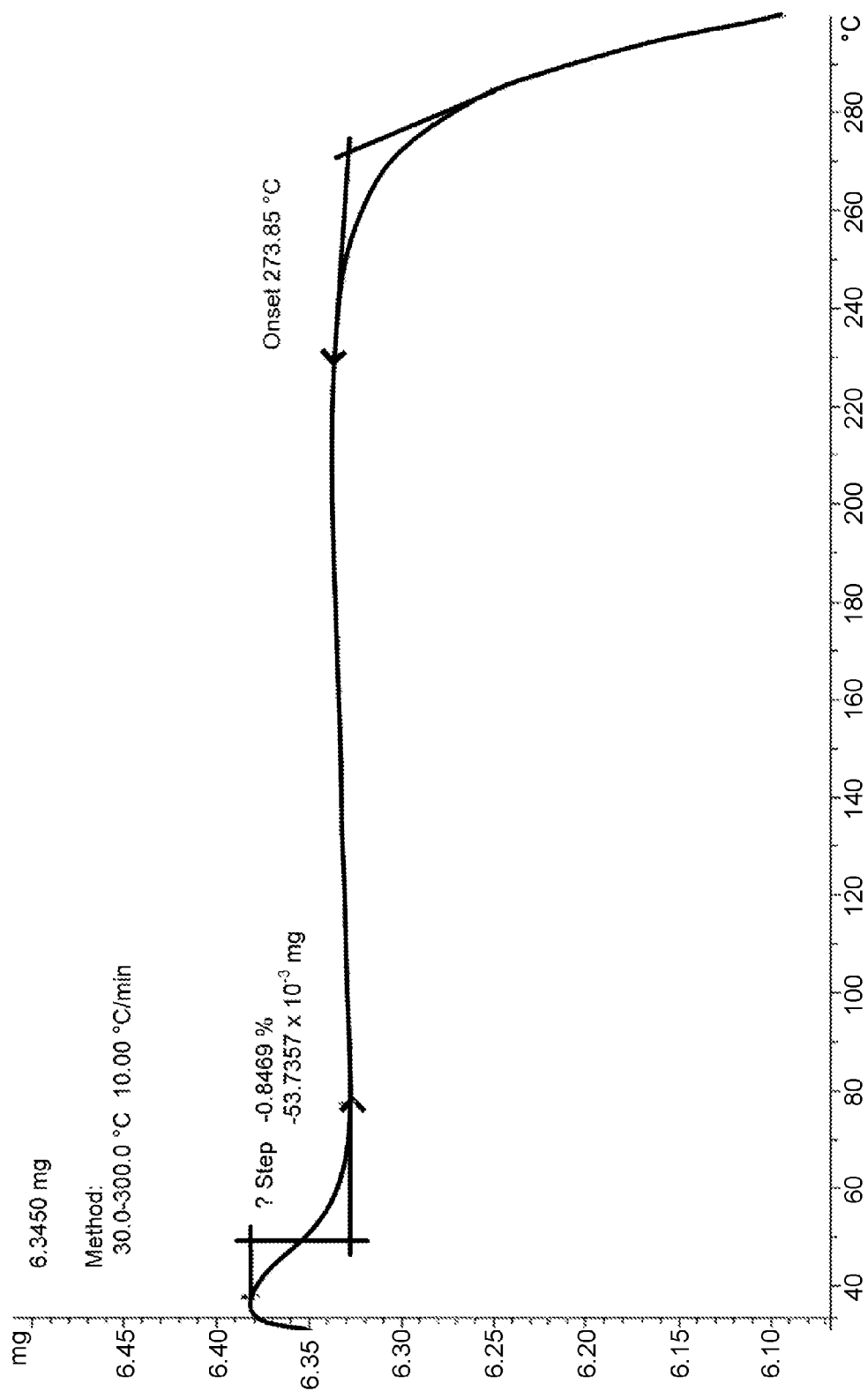
FIG. 10 is a TGA thermogram of the polymorphic Shifted Form F of compound (I).

In a further embodiment of the invention, the crystalline variable hydrate of Compound (I), Shifted Form F, has a TGA curve substantially the same as that shown in FIG. 10, measured under conditions as described herein.

Figure 11:
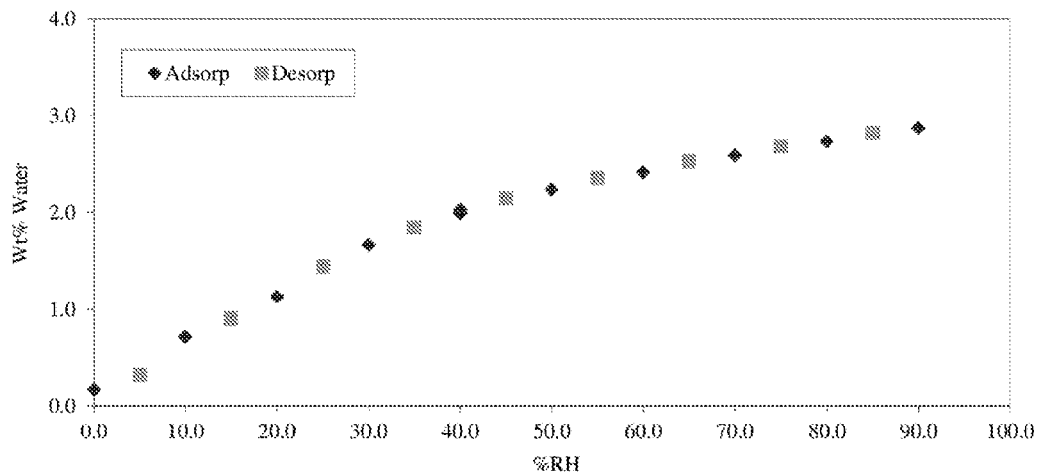
FIG. 11 is a gravimetric moisture sorption analysis of the polymorphic Shifted Form F of compound (I).
Figure 12:
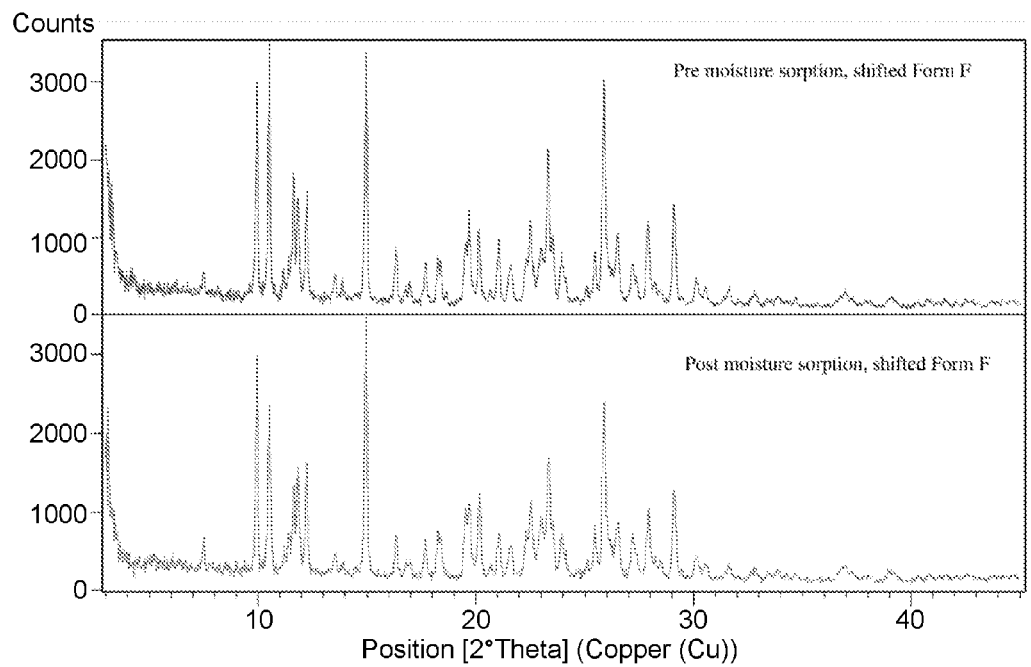
FIG. 12 shows the XRPD of the polymorphic Shifted Form F of compound (I) before and after moisture sorption analysis.

In a further embodiment of the invention, the crystalline variable hydrate of Compound (I), Shifted Form F, has a dynamic vapor sorption isotherm substantially the same as that shown in FIG. 11, measured under conditions as described herein.

Another embodiment of the invention is a pharmaceutical composition comprising a hydrate of Compound (I) (for example a crystalline variable hydrate) and at least one pharmaceutically acceptable carrier or diluent.

Another embodiment of the invention is a method for inhibiting PDE10 in a warm-blooded animal, comprising administering to the animal an effective amount of a crystalline variable hydrate of Compound (I) or pharmaceutical composition thereof.

Another embodiment of the invention is a method for treating a neurological disorder in a warm-blooded animal having said neurological disorder, comprising administering to the animal an effective amount of a crystalline variable hydrate of Compound (I) or a pharmaceutically composition thereof, wherein the neurological disorder is selected from the group consisting of psychotic disorders, anxiety disorders, Parkinson's disease, Huntington's disease, Alzheimer's disease, encephalitis, phobias, epilepsy, aphasia, Bell's palsy, cerebral palsy, sleep disorders, pain, Tourette's syndrome, schizophrenia, delusional disorders, bipolar disorders, post-traumatic stress disorders, drug-induced psychosis, panic disorders, obsessive-compulsive disorders, attention-deficit disorders, disruptive behavior disorders, autism, depression, dementia, epilepsy, insomnias and multiple sclerosis.

In a further embodiment of the invention, the neurological disorder is schizophrenia.

In a further embodiment of the invention, the neurological disorder is post-traumatic stress disorder.

Other alternative embodiments are directed to a quantity of a crystalline form of Compound (I) (for example a crystalline variable hydrate form) wherein at least about 50%, at least about 75%, at least about 95%, at least about 99%, or about 100%, of said substance is present in crystalline Form F as characterized by any of the abovementioned embodiments as defined by their XRPD spectra. The presence of such amounts of a hydrate of Compound (I), Form F, is typically measurable by XRPD analysis of the compound.

Additional embodiments are directed to a pharmaceutical composition including a hydrate of Compound (I) and a pharmaceutically acceptable carrier or diluent, wherein at least about 50%, at least about 75%, at least about 95%, at least about 99%, or about 100%, of said variable hydrate of Compound (I), Form F, in the composition is present in crystalline Form F as characterized by any of the above-mentioned XRPD spectrum defined embodiments.

The present invention provides a process for the preparation of a crystalline form of Compound (I), Form F, which includes crystallizing a hydrate of Compound (I) from a solution in solvents under conditions which yield the crystalline form of Compound (I), Form F. The precise conditions under which the crystalline form of Compound (I), Form F, is formed may be empirically determined, including the methods which have been found to be suitable in practice as described herein. As one of skill in the art will appreciate, in each of the following synthetic processes, the recited steps may (i) occur individually or one or more steps may combined into a single step, (ii) occur in the order recited or in an alternative order and (iii) occur optionally.

It has been found that the variable hydrate of Compound (I), Form F, may be prepared by a process selected from the group consisting of cooling, crash precipitation, drying, evaporation, wet grinding, melt/cool, RH stress, slurry, vapor diffusion, and vapor stress. The process of forming the hydrate of Compound (I), Form F, is also an embodiment of the present invention:

Cooling

Suspensions or solutions of Compound (I) were prepared at elevated temperatures. In some cases a distillation step was included in an attempt to remove residual water. Samples were filtered into warm receiving vials. Solutions were allowed to cool down either by turning the heating device off while keeping the sample on the hot plate (slow cool, SC) or by removing the sample from the hot plate and exposing to ambient conditions (fast cool, FC) or quickly transferring to sub-ambient conditions (crash cool, CC). Solids were collected by vacuum filtration and analyzed.

Crash Precipitation

Suspensions or solutions of Compound (I) were prepared in various solvents and filtered to remove any undissolved solids. An excess of an anti-solvent was added to the solution while stirring to precipitate solids. Solids were allowed to slurry briefly before isolation by vacuum filtration.

Drying

Select Compound (I) samples were placed in vials that were uncapped and placed under vacuum at ambient or elevated temperatures or exposed to desiccant (P2O5) at room temperature. Experiments were conducted at listed temperatures.

Evaporation

Suspensions or solutions of Compound (I) were prepared in various solvents and filtered to remove any undissolved solids. Samples were uncapped and covered in foil with small holes to allow for slow evaporation (SE) at room temperature. Samples were allowed to evaporate to dry solids unless otherwise indicated as a partial evaporation (PE). Solids were collected via vacuum filtration of the partial evaporation experiment before being analyzed.

Wet Grinding

A sample of Compound (I) was transferred to an agate milling container. An agate milling ball was added to the container and a small amount of water was added. The milling container was then attached to a Retsch mill. The sample was milled for 15 minutes at 25 Hz before the solids were scraped down from the walls of the container and milled again for another 15 minutes. The resulting solids were transferred to a new clean vial and analyzed.

Melt/Cool

Samples of Compound (I) were placed on a hot plate and heated to >160° C. Samples were held until melting of the sample was judged visually to be complete. Samples were allowed to cool under different conditions (see cooling section above) to generate different materials.

RH Stress

A sample of Compound (I) was placed in a vial, which was then uncapped and placed inside a jar containing a saturated aqueous potassium sulfate solution that was used for ~97% RH1. The experiment was conducted at room temperature.

Slurry

Suspensions of Compound (I) were prepared by adding solvent such that excess solids remained. The suspensions were then agitated in a sealed vial at the specified temperature. After the specified amount of time, the solids were isolated by vacuum filtration. Interconversion slurries were prepared by preparing a saturated solution of Compound (I) Form F by adding excess solids and stirring for ~30 minutes. Seeds of Material G were added and the sample was stirred for the specified time at the specified temperature.

Vapor Diffusion

Suspensions or solutions of Compound (I) were prepared in various solvents and filtered to remove any undissolved solids. Solutions were placed in small vials, left uncapped, and placed into a larger vial containing an anti-solvent. The larger vial was capped to allow vapor diffusion to occur. Solids were collected by decanting the liquid phase or vacuum filtration prior to analysis.

Vapor Stress

A sample of melt/cool Compound (I) (see above) was placed in a vial, which was then uncapped and placed inside a larger vial containing solvent. The experiment was conducted at room temperature.

Pharmaceutical Compositions and Methods

The aforementioned polymorphic forms of Compound (I), including Form F are useful as PDE10 inhibitors. These forms are therefore useful in the inhibition of PDE10 in a warm-blooded animal and can be used for the preparation of a pharmaceutical composition for inhibiting PDE10 activity. The appropriate dosage amounts and regimens for a particular patient can be determined by methods known in the art and by reference to the disclosure in WO 2011/112828. Generally, a therapeutically effective amount for the inhibition of PDE10 activity in a human is administered. In one embodiment, about 50 mg to 1000 mg, more preferably from about 50 mg to about 400 mg, of Compound (I) is administered per adult human per day in single or multiple doses.

Specific optimal dosage and treatment regimens for any particular patient will of course depend upon a variety of factors, including the age, body weight, general health status, sex, diet, time of administration, rate of excretion, drug combination, the severity and course of the infection, the patient's disposition to the infection and the judgment of the treating physician. In general, the compound is most desirably administered at a concentration level that will generally afford effective results without causing any harmful or deleterious side effects.

The crystalline Form F of Compound (I) at a selected dosage level is typically administered to the patient via a pharmaceutical composition. See, e.g., the description in WO 2011/112828 for the various types of compositions that may be employed in the present invention. The pharmaceutical composition may be administered orally, parenterally or via an implanted reservoir. The term parenteral as used herein includes subcutaneous, intracutaneous, intravenous, intramuscular, intra-articular, intrasynovial, intrasternal, intrathecal, and intralesional injection or infusion techniques. In certain specific embodiments, the crystalline Form F of Compound (I) is administered orally or by injection.

In some embodiments, the pharmaceutical compositions of this invention contain any conventional non-toxic pharmaceutically-acceptable carriers, diluents, adjuvants, excipients or vehicles. In some embodiments, the pH of the formulation is adjusted with pharmaceutically acceptable acids, bases or buffers to enhance the stability of the formulated compound or its delivery form.

In one embodiment, the pharmaceutical composition is in the form of a sterile injectable preparation, for example, as a sterile injectable aqueous or oleaginous suspension. This suspension is formulated according to techniques known in the art using suitable dispersing or wetting agents (such as, for example, Tween 80) and suspending agents.

In certain embodiments, the pharmaceutical compositions is in the form of separate oral pharmaceutical compositions including the crystalline Form F of the variable hydrate of Compound (I) and at least one pharmaceutically acceptable carrier or diluent. Exemplary orally acceptable dosage forms for the oral pharmaceutical compositions include, but are not limited to, tablets, capsules (e.g., hard or soft gelatin capsules), including liquid-filled capsules, spray dried granules, hot melt granules, and aqueous suspensions and solutions. In the case of tablets for oral use, carriers which are commonly used include lactose, microcrystalline cellulose and corn starch. Lubricating agents, such as magnesium stearate, are also typically added. For oral administration in a capsule form, useful diluents include lactose, microcrystalline cellulose and dried corn starch. Examples of soft gelatin capsules that can be used include those disclosed in U.S. Pat. No. 5,985,321. When aqueous suspensions are administered orally, the active ingredient is combined with emulsifying and suspending agents. If desired, certain sweetening and/or flavoring and/or coloring agents may be added.

Other suitable vehicles or carriers for the above noted formulations and compositions can be found in standard pharmaceutical texts, e.g., in "Remington's Pharmaceutical Sciences", 19th ed., Mack Publishing Company, Easton, Pa., 1995.

Certainly, when the crystalline Form F of the variable hydrate of Compound (I) is formulated in a liquid vehicle, for example, as a liquid oral solution including for example liquid-filled capsules or suspension as amorphous spray dry powder for oral administration or solution by injection, the crystalline Form F of the variable hydrate of Compound (I) loses its crystalline nature. It was only by discovering a method for preparing the variable hydrate of Compound (I) in a stable crystalline form that the present inventors enabled efficient pharmaceutical processing and pharmaceutical formulation manufacture using the variable hydrate form.

Methods of Characterization

X-Ray Powder Diffraction

XRPD patterns were collected with a PANalytical CubiX-Pro XRD diffractometer using an incident beam of Cu radiation produced using an Optix long, fine-focus source. An elliptically graded multilayer mirror was used to focus CuKα X-rays (1.54 Å) through the specimen and onto the detector. Prior to the analysis, a silicon specimen (NIST SRM 640d) was analyzed to verify the observed position of the Si 111 peak is consistent with the NIST-certified position. A specimen of the sample was sandwiched between 3-μm-thick films and analyzed in transmission geometry. A beam-stop, short antiscatter extension, and antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b. The tube power was set to 45 kV and 40 mA. Step scans were run from 3.0 to 45.0° 2θ, at 0.02° per step, 10 seconds per step.

Differential Scanning calorimetry (DSC)

DSC was performed using a TA Instruments 2920 differential scanning calorimeter. Temperature calibration was performed using NIST-traceable indium metal. DSC analysis was performed on each sample "as is". The sample was placed into an aluminum DSC pan, covered with a pierced lid, crimped, and the weight was accurately recorded. A weighed aluminum pan configured as the sample pan was placed on the reference side of the cell. The differential scanning calorimetry curve was obtained on a sample heated from 30° C. to 300° C. ramped at 10° C. per minute.

Thermogravimetric Analysis (TGA)

TG analyses were performed using a TA Instruments 2950 thermogravimetric analyzer. Temperature calibration was performed using nickel and Alumel™. Each sample was placed in an aluminum or platinum pan and inserted into the TG furnace. The furnace was heated under a nitrogen purge. The thermal gravimetric curve was obtained on a sample heated from 30° C. to 300° C. ramped at 10° C. per minute.

Dynamic Vapor Sorption (DVS)

Gravimetric moisture sorption experiments were carried out on all materials by first holding the sample at 40% RH and 25° C. until an equilibrium weight was reached or for a maximum of four hours. The sample was then subjected to an isothermal (25° C.) adsorption scan from 40 to 90% RH in steps of 10%. The sample was allowed to equilibrate to an asymptotic weight at each point for a maximum of four hours. Following adsorption, a desorption scan from 85 to 5% RH (at 25° C.) was run in steps of −10%, again allowing a maximum of four hours for equilibration to an asymptotic weight. An adsorption scan was then performed from 0% RH to 40% RH in steps of +10% RH. The sample was then dried for no less than two hours at 60° C. and the resulting solid analyzed by XRPD.

Karl Fischer (KF) Titration

Coulometric Karl Fischer (KF) analysis for water determination was performed using a Mettler Toledo DL39 KF titrator. A blank titration was carried out prior to analysis. The sample was prepared under a dry nitrogen atmosphere, where ~21-22 mg of the sample were extracted in approximately 1 mL dry Hydranal—Coulomat AD in a pre-dried vial. The supernatant was added to the KF coulometer through a septum and mixed for 10 seconds. The sample was then titrated by means of a generator electrode, which produces iodine by electrochemical oxidation: $2I^- \rightarrow I_2 + 2e^-$. Two replicates were obtained to ensure reproducibility.

Nuclear Magnetic Resonance (NMR)

Samples were dissolved in DMSO-$d_6$ with 0.05% tetramethylsilane (TMS) for internal reference. $^1$H-NMR spectra were acquired at 500 MHz using 5 mm broadband ($^1$H-X) Z gradient probe. A 30 degree pulse with 20 ppm spectral width, 1.0 s repetition rate, and 32 transients were utilized in acquiring the spectra.

EXAMPLES

In order that this invention to be more fully understood, the following examples are set forth. These examples are for the purpose of illustrating embodiments of this invention, and are not to be construed as limiting the scope of the invention in any way. The reactants used in the examples below may be obtained either as described herein, or if not described herein, are themselves either commercially available or may be prepared from commercially available materials by methods known in the art. Certain starting materials, for example, may be obtained by methods described in the International Patent Applications WO 2011/112828.

Unless otherwise specified, solvents, temperatures, pressures, and other reaction conditions may be readily selected by one of ordinary skill in the art. Typically, reaction progress may be monitored by High Pressure Liquid Chromatography (HPLC), if desired, and intermediates and products may be purified by chromatography on silica gel and/or by recrystallization.

Abbreviations or symbols used herein include:

Ac: acetyl; AcOH: acetic acid; Ac2O: acetic anhydride; Bu: butyl; DMAc: N,N-Dimethylacetamide; ee: enantiomeric excess; Eq: equivalent; Et: ethyl; EtOAc: ethyl acetate; EtOH: ethanol; GC: gas chromatography; HPLC: high performance liquid chromatography; IPA: isopropyl alcohol; IPAc: isopropyl acetate; iPr or i-Pr: 1-methylethyl (iso-propyl); KF: Karl Fischer; LOD: limit of detection; Me: methyl; MeCN: acetonitrile; MeOH: methanol; MS: mass spectrometry (ES: electrospray); MTBE: methyl-t-butyl ether; BuLi: n-butyl lithium; NMR: nuclear magnetic resonance spectroscopy; Pr: propyl; tert-butyl or t-butyl: 1,1-dimethylethyl; TFA: trifluoroacetic acid and; THF: tetrahydrofuran.

Example 1

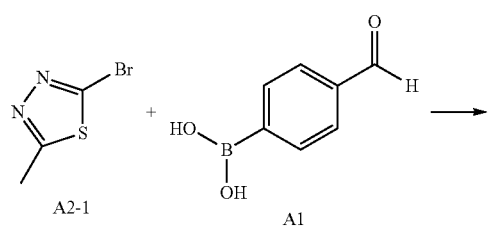

A mixture of 2-bromo-5-methyl-1,3,4-thiadiazole A2-1 (13.1 g, 73.3 mmol), (4-formylphenyl)boronic acid A1 (10.0 g, 66.7 mmol), 2M K$_3$PO$_4$ (66.7 mL, 133.4 mmol) in toluene (150 mL) and ethanol (38 mL) was heated to 55° C. under nitrogen then degassed by alternately putting under vacuum and nitrogen three times for several minutes each. Tetrakis(triphenylphosphine)palladium (1.54 g, 1.33 mmol) was added, and then the mixture was degassed again. After heating for 18 hours at 80° C. and cooling to room temperature, the aqueous layer was separated. The mixture was washed with brine and the remaining organic layer was reduced in volume by distillation. Addition of heptane provided a solid which was collected by filtration to give 4-(5-methyl-1,3,4-thiadiazol-2-yl)benzaldehyde B1-1 as a solid in 85% yield.

Example 2

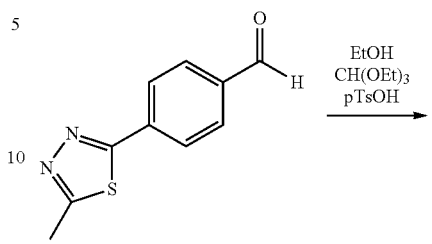

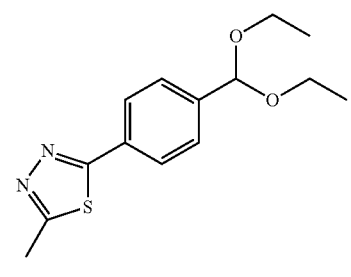

B1-1 (1.05 g, 5.14 mmol), EtOH (10 mL), CH(OEt)$_3$ (1.1 equiv), and para-toluenesulfonic acid monohydrate (5 mol %) were heated at 67° C. for 30 minutes. The solution was cooled, and saturated aqueous NaHCO$_3$ (10 mL) was added. The mixture was transferred to a separatory funnel with dichloromethane (20 mL). Additional water dissolved the solids and the layers were separated. The organic layer was concentrated under reduced pressure to give a mixture of solids and oil. The mixture was redissolved in dichloromethane (10 mL) and the solution was washed with water (5 mL). Solvent removal gave C1-1 (1.29 g, 90% yield).

Example 3

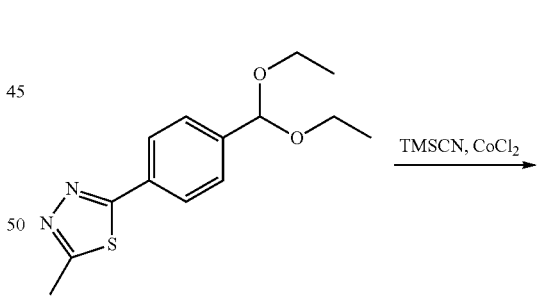

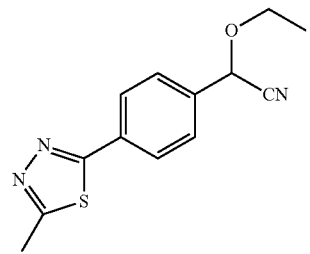

C1-1 (145 mg, 0.522 mmol) was stirred with TMSCN (100 µL, 1.5 equiv) and dichloroethane (1 mL) while CoCl$_2$ (5 mg) was added. The reaction was heated at 60° C. for 3.25 hours. Saturated aqueous NaHCO$_3$ (2 mL) and dichloromethane (5 mL) were added. The layers were separated and the organic layer was concentrated under reduced pressure to give D1-1 as an off-white solid (104 mg, 77% yield).

Example 4

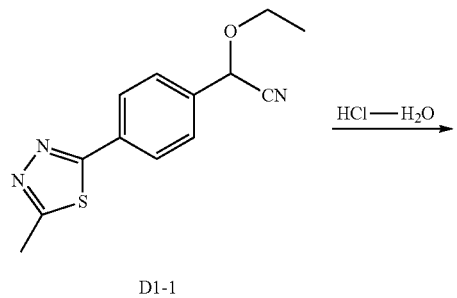

D1-1

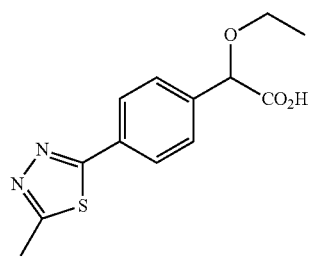

E1-1

A mixture of D1-1 (1.01 g, 3.90 mmol), 1,2-dichloroethane (5.0 mL), concentrated HCl (2.0 mL) and water (1.0 mL) were heated to 70° C. for 15 hours. After cooling to room temperature, water (1 mL) was added. The organic phase was separated and additional water (5 mL) was added to the aqueous layer then extracted with dichloromethane (2×10 mL). The first organic phase was combined with the dichloromethane extracts and the mixture was concentrated under reduced pressure to provide E1-1 as a tan solid (1.02 g, 94% yield).

Example 5

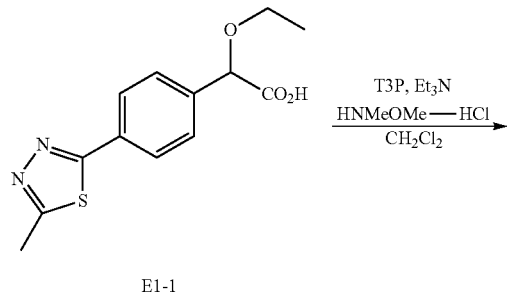

E1-1

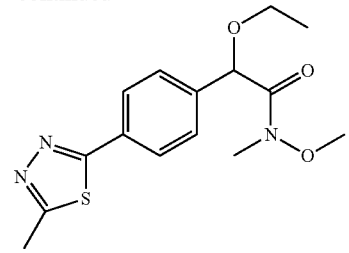

F1-1

To a reactor was charged E1 (117.2 g, 0.392 mol as hydrate, 6.3% water) with N,O-dimethylhydroxylamine hydrochloride (61.5 g, 1.5 equiv) and dichloromethane (936 mL). The mixture was stirred to Form F slurry. Triethylamine (272 mL) was charged slowly over 15 minutes, resulting in a slight exotherm. Propylphosphonic anhydride ("T3P") (376 g as 50 wt % solution in dichloromethane, 1.5 equiv) was charged slowly over 1 hour. Water (470 mL) was charged over 10 minutes. The layers were separated and the aqueous phase was extracted with dichloromethane. The organic phases were combined and washed with saturated sodium bicarbonate solution, and 1N HCl solution. The batch was concentrated somewhat under reduced pressure. Isopropyl acetate was added, and the mixture was slightly concentrated again under reduced pressure. This was repeated twice. The mixture was heated, seeded at 50° C., heptane was added then it was cooled to room temperature. The solid was collected by filtration and washed with a mixture of isopropylacetate-heptane. F1-1 was obtained in 88% yield and purity of 99%.

Example 6

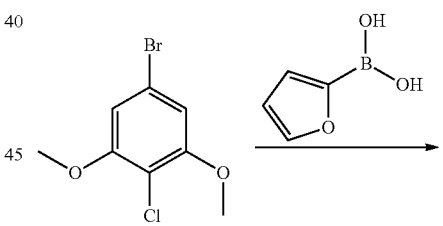

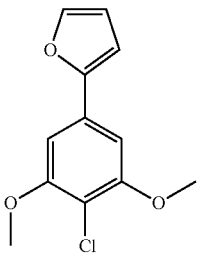

G1-1

2-(4-Chloro-3,5-dimethoxyphenyl)furan G1-1 was synthesized according to the procedure reported in International PCT Application Publication No. WO 2008/040669 as follows. To a flask containing 3,5-dimethoxy-4-chloro-bromobenzene (5 g, 20 mmol), 2-furylboronic acid (2.45 g, 21.9 mmol), and 2M Na$_2$CO$_3$ (25 mL) was added tetrahydrofuran (50 mL). The mixture was degassed by alternately putting under house vacuum and nitrogen three times for several minutes each. Tetrakis(triphenylphosphine)palladium (0.46 g, 0.4 mmol) was added and the mixture was degassed again then heated at 60° C. for 17 hrs. Volatiles were removed in vacuo then methanol (10 mL) was added and the slurry was stirred at 60° C. for 2 h. The mixture was cooled to room temperature, and the solids were collected. The solid was slurried in hot methanol then filtered and dried to give 2-(4-chloro-3, 5-dimethoxyphenyl) furan (3.18 g, 67% yield).

Example 7

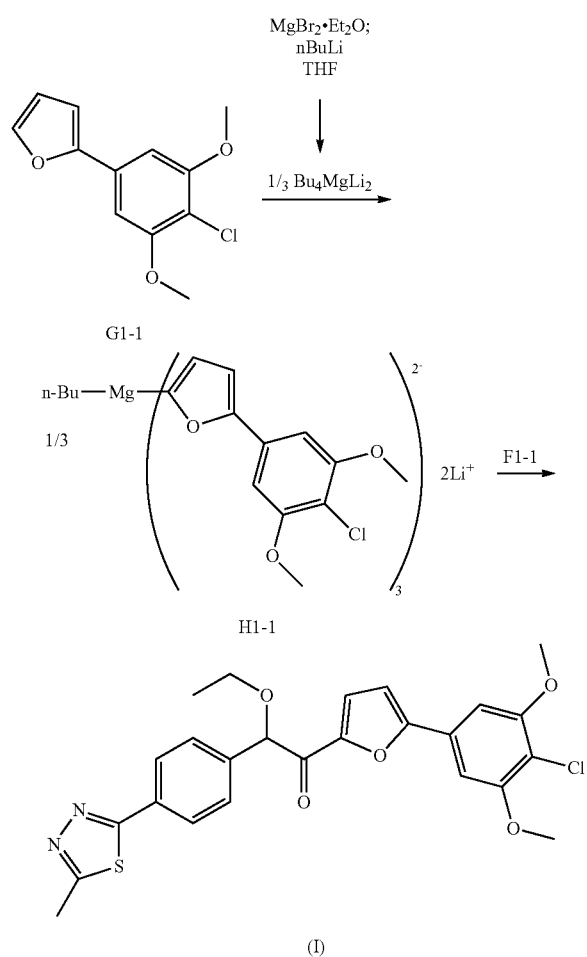

To a nitrogen purged 50 L jacketed vessel was charged nitrogen sparged THF (8.9 L). With agitation, MgBr$_2$.Et$_2$O (899 g, 3.48 mol) was added which caused an exotherm as solids dissolved and reprecipitated. The batch was cooled to −13° C. and n-BuLi (3.625 kg, 13.9 mol, 24.6% in hexanes) was added over 90 min at −13 to −7° C. to give a solution. At −8 to −11° C., a solution of G1-1 (2.651 kg, 11 mol) in nitrogen-sparged THF (7.98 L) was added over 66 min at −8 to −11° C. and rinsed in with a THF rinse (0.99 L) to give a solution. The temperature of the batch was increased to 15° C. over 35 min and the batch was agitated for 1.25 hours at 15 to 20° C. The solution of H1-1 was stored sealed with a bubbler attached to relieve any excess pressure (no N$_2$ flow) overnight at 20° C.

To a nitrogen purged 100 L jacketed vessel was charged F1-1 (3.00 kg, 12.58 mol) and toluene (24.0 L). The slurry was sparged with nitrogen for 1.75 hours, and nitrogen-sparged THF (6.0 L) was added. The batch was heated to 35° C. to afford a solution then cooled to −17° C. The H1-1 solution was added at −17 to −21° C. over 92 min. Toluene (150 mL) was used to rinse the lines to the reactor. A chilled solution of acetic acid (1.74 L) in water (5.34 L) was added over 24 minutes at −23 to −13° C. to give a slurry. After warming to 0° C., additional water (10.7 L) was added over 23 min at 0 to 8° C. The batch was heated to 41° C. to give a two phase mixture. The aqueous phase (18 L) was removed. To the organic (58 L) was added water (16.0 L). The batch was heated to 42° C. for 15 min then the aqueous phase was removed.

After stirring overnight at 20° C., the slurry was reheated to 58° C. to dissolve the solids. Vacuum was applied and the volume reduced to 30 L. The batch was cooled to 45° C. Water (750 mL) was added, followed by seed crystals (21 g). The slurry was held for 2 h at 40° C., cooled over 3 h to 20° C., held for 12 h, and finally cooled to 5° C. over 1 h and held overnight. The product was collected by filtration, washed with toluene and dried to yield 3.18 kg compound I (98.2% purity).

Example 8

Crystallization of Form F

Compound (I) was crystallized using a variety of techniques. Experiments were performed on medium scale (~40-110 mg) utilizing a variety of solvents. Specific details can be found in Table 2 below.

TABLE 2

| Solvent (vol:vol) | Conditions |
|---|---|
| Acetone (Anhydrous) | Compound (I) melted, fast cooled, and stored over P$_2$O$_5$ for about 2 days prior to use. Slurry in solvent at room temperature for about 3 hours. |
| Acetone (Anhydrous):MTBE 1:3 | Crash precipitation at room temperature (solution); slow evaporation at room temperature. |
| Acetone (Anhydrous):Water 1:1 | Slurry at room temperature for about 6 days. |
| Acetone (Anhydrous):Water 1:1 | Slurry for about 30 min at room temperature; seed with Material G; slurry for about 3 days at room temperature. |
| Acetone (Anhydrous):Water 1:1 | Slurry at sub-ambient temperature (~2-8° C.) for about 4 days. |
| Acetone (Anhydrous):Water 1:3 | Crash precipitation at room temperature. |
| Acetone:Water 9:1 | Slurry at room temperature for about 6 days. |
| ACN:Water 3:4 | Crash precipitation at room temperature. |
| 2-BuOH | Slow evaporation in anhydrous acetone; slurry in 2-BuOH at room temperature for about 6 days. |
| EtOAc:MTBE 1:2 | Crash precipitation at room temperature (solution); partial evaporation at room temperature. |
| EtOH:Water 1:1 | Crash precipitation at about 74° C.; filter while warm. |
| IPA | Slow cool from a about 76° C. to about 53° C. and hold for about 1 hour (ppt); hold for another 30 minutes, slow cool to room temperature. |

TABLE 2-continued

| Solvent (vol:vol) | Conditions |
|---|---|
| IPrOAc | Distill at about 84° C. for about 3 hours; slow cool to room temperature; slurry about 1 day at room temperature. |
| MeOH | Slurry at room temperature for about 6 days. |
| MeOH (Anhydrous) | Compound (I) melted, fast cooled, and stored over $P_2O_5$ for about 2 days prior to use. Slurry at room temperature for about 3 hours. |
| MeOH:Water 95:5 | Compound (I) melted, fast cooled, and stored over $P_2O_5$ for about 2 days prior to use. Slurry at room temperature for about 3 hours. |
| MeOH:Water 90:10 | Compound (I) melted, fast cooled, and stored over $P_2O_5$ for about 2 days prior to use. Slurry at room temperature for about 3 hours. |
| MEK | Slow evaporation from THF at room temperature; slow evaporation with MEK at room temperature. |
| MTBE | Compound (I) melted and slow cooled; vapor stress at room temperature for about 3 days. |
| MTBE:Heptane 1:1 | Compound (I) melted and crash cooled; Slurry with solvent at room temperature for about 3 days. |
| 1-PrOH | Slurry at about 60° C. for about 1 day. |
| THF:Heptane 1:2 | Slurry at room temperature for about 6 days. |
| THF:Toluene 1:1 | Slurry at sub-ambient temperature for about 4 days. |
| Toluene | Slurry at room temperature for about 6 days. |
| Toluene | Compound (I) melted, fast cooled, and stored over $P_2O_5$ for about 2 days prior to use. Slurry in solvent at room temperature for about 3 hours. |
| Toluene | Slow cool from about 80° C. (solution); stir at room temperature for about 4 days. |
| Toluene | Crash cool from about 80° C. |
| Toluene | Partial evaporation at room temperature. |
| Water | Wet grinding for 2 cycles of 25 Hz for 15 minutes. |
| Water | Slurry at room temperature for about 6 days. |
| Water | Slurry at room temperature for 30 minutes, seed with Material G, slurry for about 3 days at room temperature. |
| Water | Slurry at room temperature for 30 minutes, seed with Material G, slurry for about 3 days at sub-ambient temperature. |

Example 9

X-Ray Indexing Solution of the Variable Hydrate of Compound (I), Form F

The XRPD pattern of the hydrate of Compound (I), Form F, is shown in FIG. 24. The XRPD pattern was successfully indexed using propriety software, indicating the samples are composed primarily of the same single crystalline phase. Different indexing solutions of XRPD patterns can result in slight variations to the unit cell parameters. Indexing solutions within ±10 percent of the results shown in Table 3 also comprise the crystal structure of Compound (I), Form F.

TABLE 3

Crystal structure parameters for variable hydrate of Compound (I) Form F

| Temperature | 90(2)K |
| Wavelength | 1.54178 Å |
| Crystal system | Tetragonal |
| Space group | P2$_1$/c |

TABLE 3-continued

Crystal structure parameters for variable hydrate of Compound (I) Form F

| Unit cell dimensions | a = 8.655 Å | α = 90° |
| | b = 17.893 Å | β = 102.67° |
| | c = 16.315 Å | γ = 90° |
| Volume | 2465.1 Å$^3$ | |
| Theta range for data collection | 1.00 to 39.99° | |

In addition, the crystal structure results shown in Table 3 indicate that Compound (I), Form F, can accommodate up to one mole of water per mole of Compound (I).

Example 10

Thermal Analysis of the Hydrate of Compound (I), Form F

Figure 8:
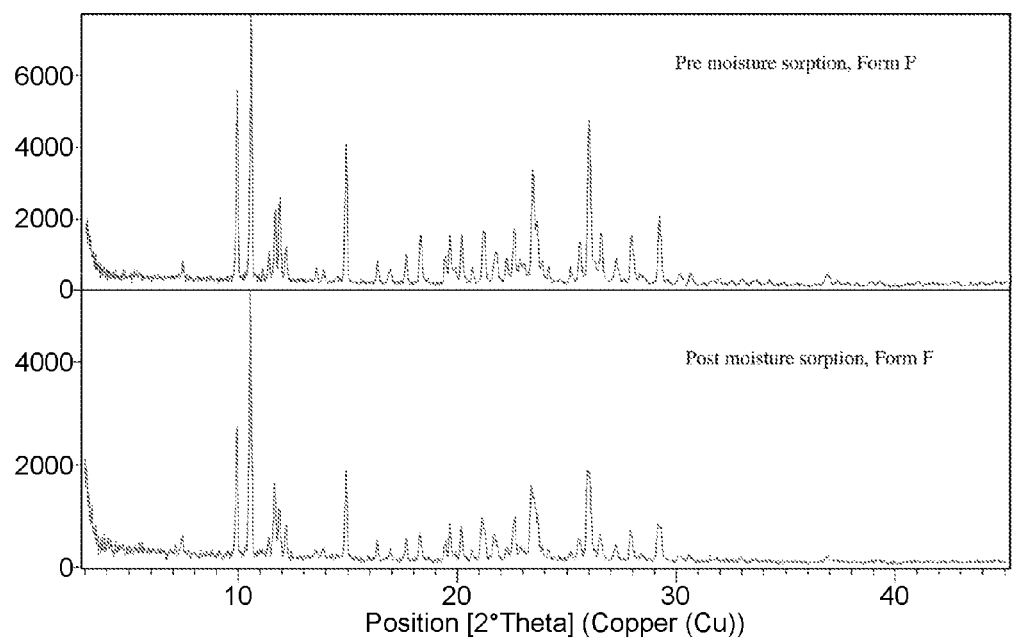
FIG. 8 shows the XRPD of the polymorphic Form F of compound (I) before and after moisture sorption analysis.

Compound (I), Form F, was further characterized by thermal analysis (DSC and TGA), Karl Fischer titration, and DVS. DSC thermogram shows a single endothermic peak at 148.5° C. (FIG. 5). TGA shows a weight loss of 0.2 wt % between 130-160° C. (FIG. 6). The weight loss observed on TGA corresponds to the melt on DSC. Moisture sorption analysis indicates Form F is moderately hygroscopic. The material absorbed 2.0 wt % moisture at 60% RH and 2.4 wt % moisture at 90% RH (FIG. 7). XRPD of the post moisture sorption sample, which was dried at 0% RH and 60° C. for 2 hours, was consistent with Form F (FIG. 8). Karl Fisher analysis of the sample indicates a moisture content of 0.6 wt %, which was performed when lab humidity was around 20% RH.

Example 11

Thermal Analysis of the Hydrate of Compound (I), Shifted Form F

Compound (I), Shifted Form F, was further characterized by thermal analysis (DSC and TGA), Karl Fischer titration, and DVS. DSC thermogram shows a broad endotherm at 59.9° C. followed by a melting endotherm at 146.7° C. (FIG. 9). TGA shows a weight loss of 0.8 wt % between 30-80° C. (FIG. 10). It is noteworthy that there is no weight loss occurring during the melt unlike Form F. Similar to Form F, moisture sorption analysis indicates shifted Form F material is moderately hygroscopic. The material absorbs 2.4 wt % moisture at 60% RH and 2.9 wt % moisture at 90% RH (FIG. 11). XRPD of the post moisture sorption sample, which was dried at 0% RH and 60° C. for 2 h, was consistent with shifted Form F. Karl Fisher analysis was performed on a shifted Form F sample and the water content was determined to be 2.4 wt %. The water content by KF is higher than the weight loss detected by TGA. It is possible that some moisture was slowly carried away by nitrogen stream and not reflected in the weight loss attributed to the thermal event. Characterization of shifted Form F was performed when lab humidity was between 50-60% RH.

Example 12

Preparation of Form A

An oven-dried flask was charged with G1-1 (1.11 g), anhydrous THF (120 mL) and TMEDA (N,N,N',N'-tetramethylethylene diamine, 0.77 mL) then cooled to −78° C. Lithium diisopropylamide (2.0 M in THF/heptane/ethylbenzene, 2.6 mL) was added and the mixture stirred at −78° C. for 1 hour. A solution of F1-1 (1.5 g) in anhydrous THF (10 mL) was added quickly and the reaction was stirred at −78° C. for 15 min then allowed to warm to 0° C. over 20-30 minutes. 1N HCl (65 mL) and EtOAc (100 mL) was added. The layers were separated, the organic layer was dried over sodium sulfate and concentrated in vacuo. Chromatography with 70% EtOAc-hexanes gave Compound (I) as a pale yellow solid.

Figure 13:
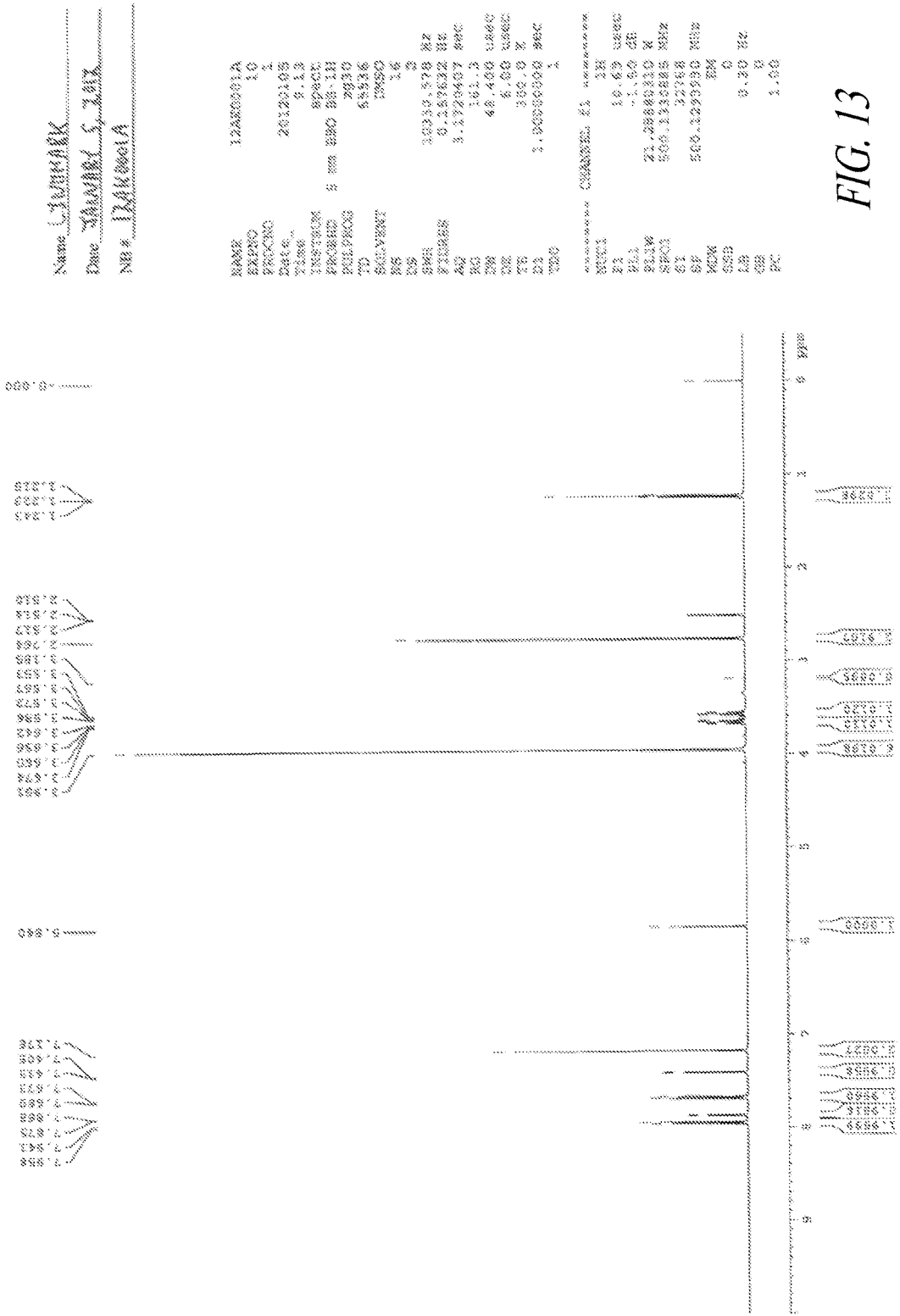
FIG. 13 is the $^1$H NMR of the polymorphic Form A of compound (I).
Figure 14:
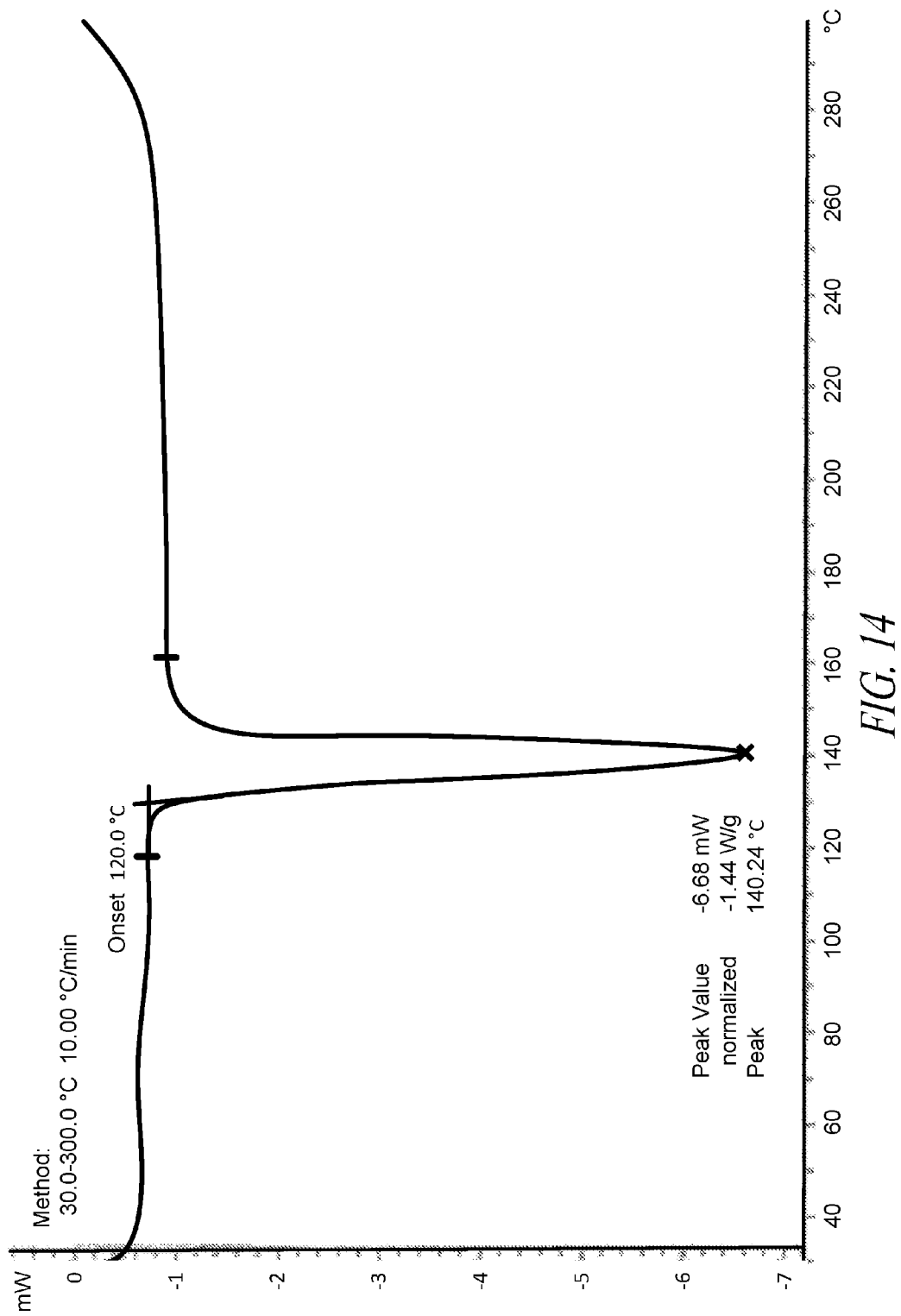
FIG. 14 is the DSC thermogram of the polymorphic Form A of compound (I).
Figure 15:
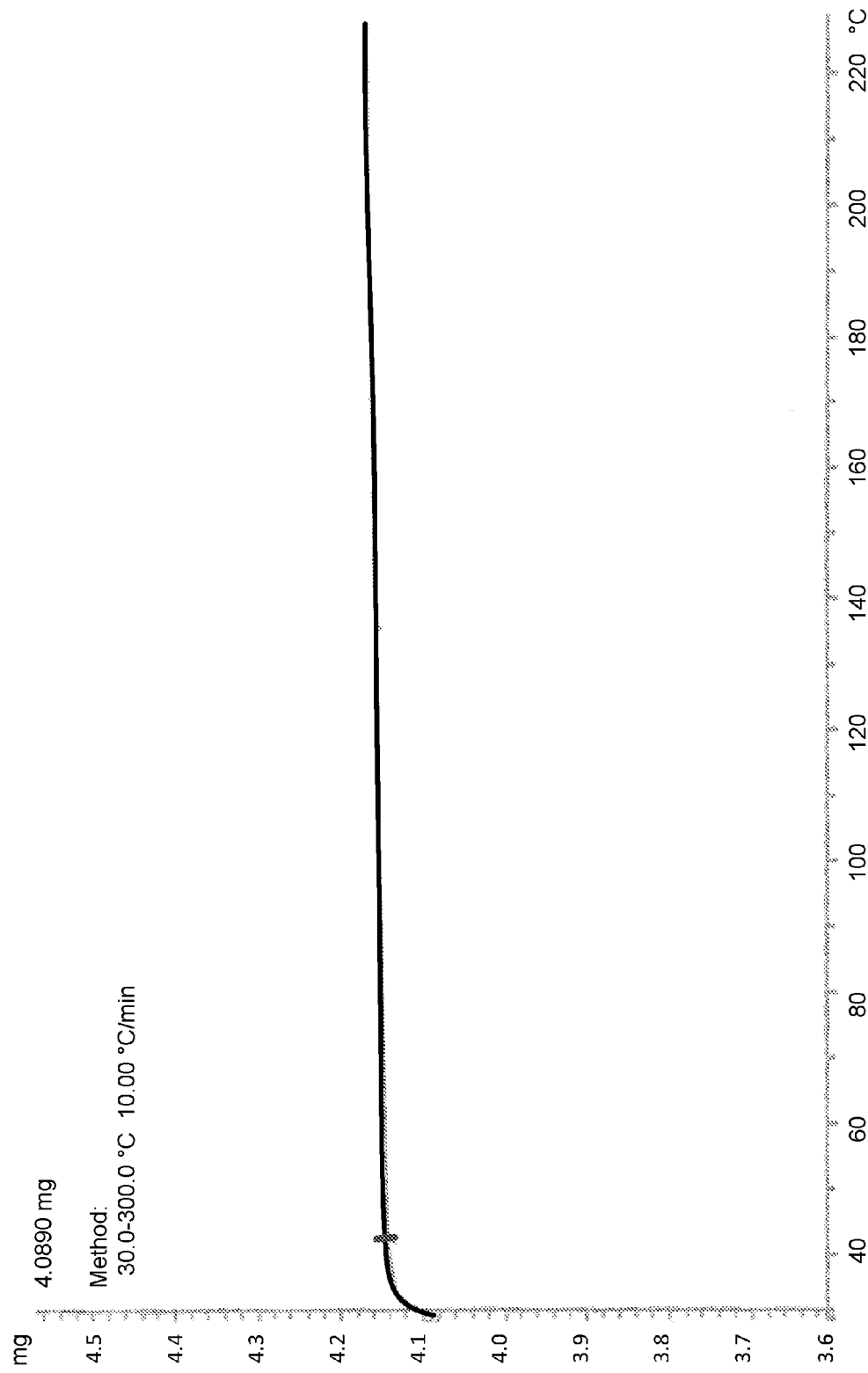
FIG. 15 is the TGA thermogram of the polymorphic Form A of compound (I).

XRPD of Form A is presented in FIG. 1. $^1$H NMR of Form A was consistent with the structure and free of residual solvents (FIG. 13). DSC indicates a single melting transition at 140.2° C. (FIG. 14). TGA shows no weight loss throughout the heating program from 30 to 230° C. (FIG. 15). Based on thermal analysis data Form A was identified as an anhydrous polymorph.

TABLE 4

XPRD Peaks of Form A
Form A of Compound (I)

| Angle 2-Theta ° | Relative Intensity % |
|---|---|
| 3.1 ± 0.2 | 8 |
| 5.6 ± 0.2 | 100 |
| 7.7 ± 0.2 | 5 |
| 8.1 ± 0.2 | 5 |
| 9.1 ± 0.2 | 4 |
| 9.9 ± 0.2 | 5 |
| 11.2 ± 0.2 | 65 |
| 11.7 ± 0.2 | 13 |
| 12.0 ± 0.2 | 6 |
| 12.7 ± 0.2 | 16 |
| 13.9 ± 0.2 | 19 |
| 14.9 ± 0.2 | 22 |
| 16.0 ± 0.2 | 43 |
| 16.3 ± 0.2 | 9 |
| 16.8 ± 0.2 | 12 |
| 17.5 ± 0.2 | 5 |
| 17.9 ± 0.2 | 6 |
| 18.3 ± 0.2 | 5 |
| 18.9 ± 0.2 | 14 |
| 20.0 ± 0.2 | 26 |
| 20.7 ± 0.2 | 10 |
| 21.4 ± 0.2 | 42 |
| 21.8 ± 0.2 | 14 |
| 22.1 ± 0.2 | 18 |
| 22.5 ± 0.2 | 16 |
| 23.3 ± 0.2 | 20 |
| 23.6 ± 0.2 | 20 |
| 24.2 ± 0.2 | 30 |
| 24.7 ± 0.2 | 7 |
| 25.2 ± 0.2 | 23 |
| 25.6 ± 0.2 | 11 |
| 26.3 ± 0.2 | 16 |
| 27.2 ± 0.2 | 5 |
| 28.2 ± 0.2 | 19 |
| 29.1 ± 0.2 | 6 |
| 29.9 ± 0.2 | 7 |
| 30.7 ± 0.2 | 4 |
| 31.3 ± 0.2 | 8 |
| 31.9 ± 0.2 | 3 |
| 33.5 ± 0.2 | 3 |
| 34.2 ± 0.2 | 2 |
| 35.0 ± 0.2 | 5 |
| 37.6 ± 0.2 | 2 |
| 39.1 ± 0.2 | 2 |

Example 13

Preparation of Form B

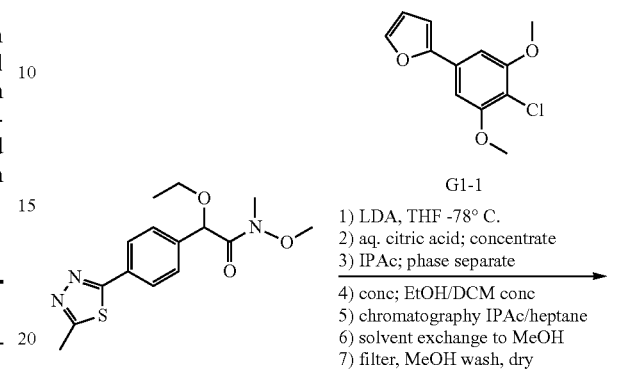

To a dry nitrogen-purged reactor, G1-1 (223 g) and anhydrous THF (19.84 kg) were charged. TMEDA (tetramethylethylene diamine, 157 mL) was added and the mixture was cooled to below −75° C. A solution of LDA in THF/heptane/ethylbenzene (1.8 M, 742 g) was quickly charged to the reactor. The mixture was stirred for 90 minutes at −75° C. then a solution of F1-1 (300 g) in anhydrous THF (1.8 L) was added quickly. The flask from which the solution was added was rinsed with additional anhydrous THF (250 mL). The mixture was stirred at −75° C. for 1 hour then warmed to 20° C. and quenched with the addition of 10% citric acid (7 L). The batch was concentrated in vacuo to approximately 10 L then the layers were separated. The organic layer was washed with brine and concentrated in vacuo. The resulting oil was redissolved in ethanol-dichloromethane and concentrated in vacuo. Chromatography with 70% isopropyl acetate-heptane gave Compound (I).

The resulting solid was slurried in methanol at 60° C. on a rotary evaporator then cooled to room temperature, isolated on a sintered funnel and rinsed with methanol to obtain Compound (I) as a purified crystalline solid. The new XRPD spectra pattern was designated Form B.

Figure 16:
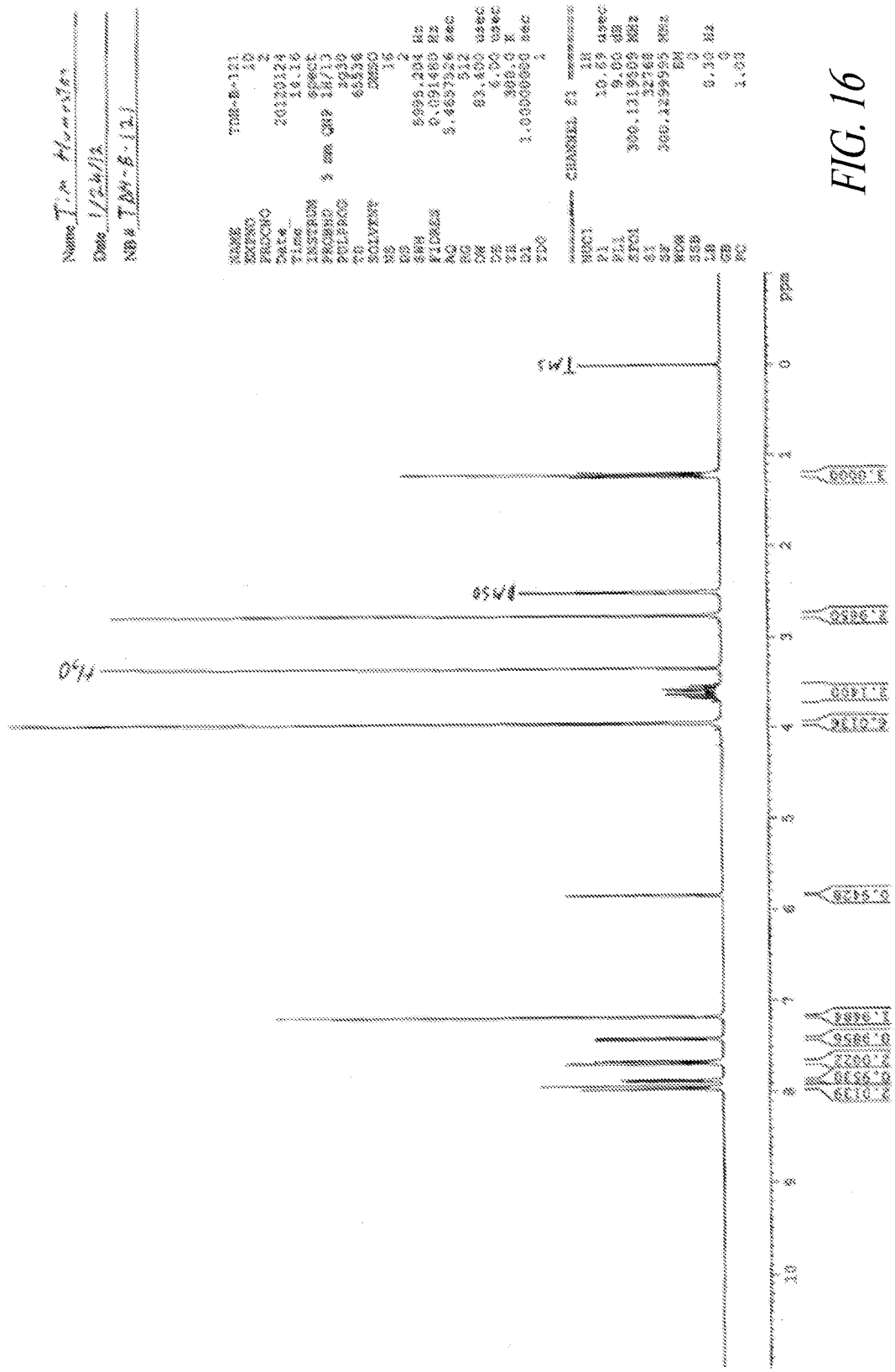
FIG. 16 is the $^1$H NMR of the polymorphic Form B of compound (I).
Figure 17:
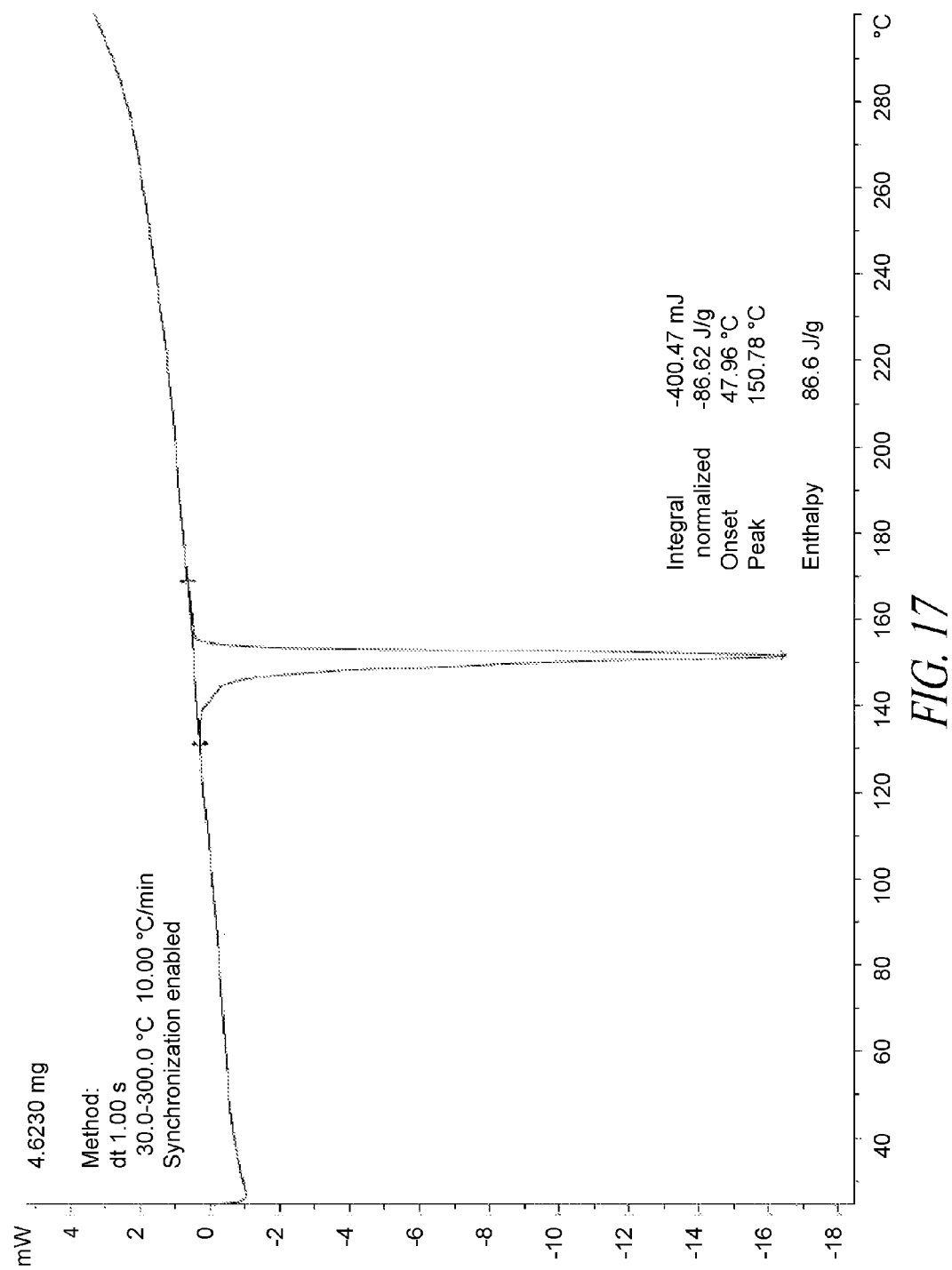
FIG. 17 is the DSC thermogram of the polymorphic Form B of compound (I).
Figure 18:
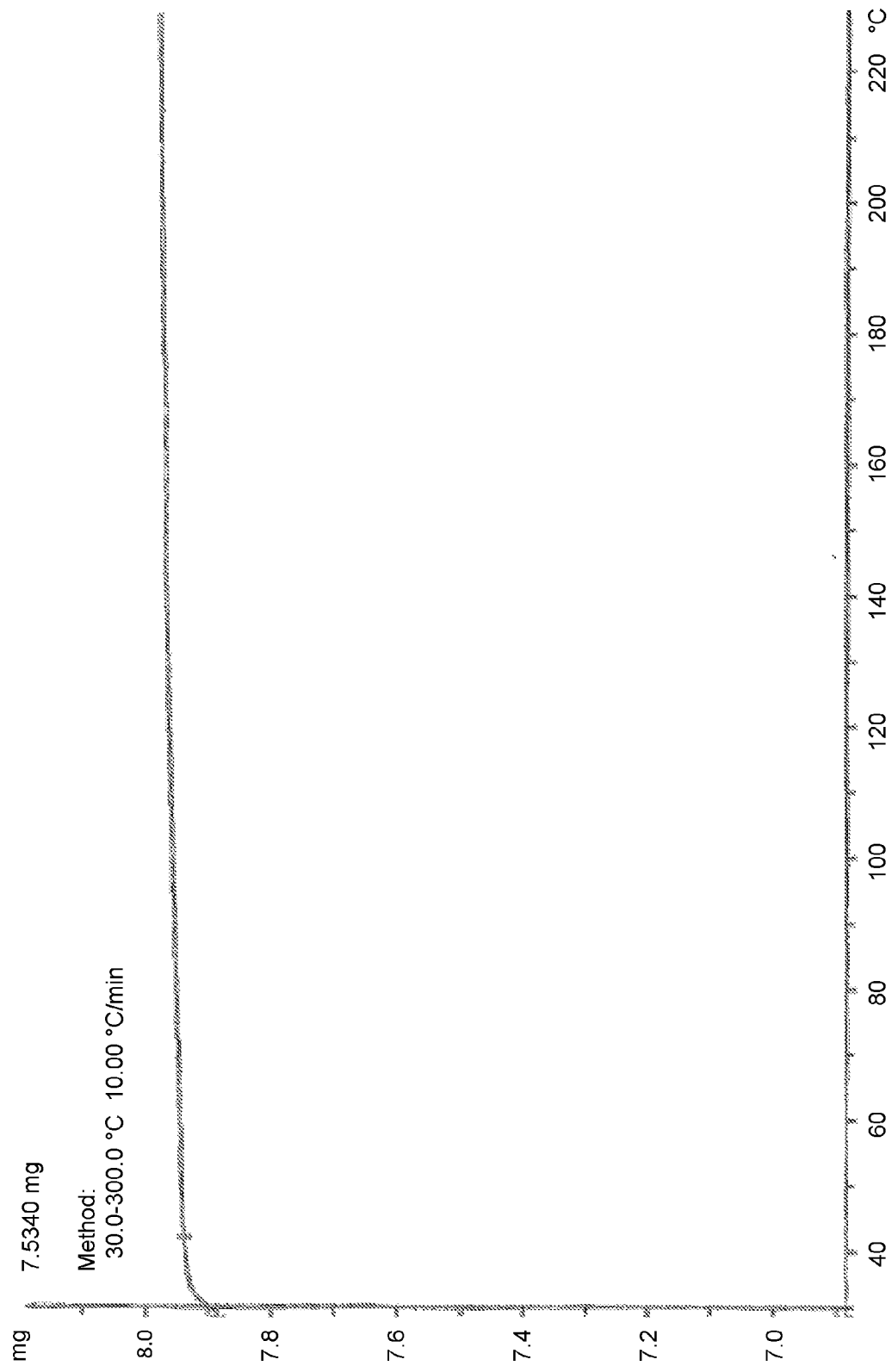
FIG. 18 is the TGA thermogram of the polymorphic Form B of compound (I).

XRPD Pattern of Form B is presented in FIG. 1. $^1$H NMR of Form B is consistent with the structure and is free of residual solvents (FIG. 16). DSC thermogram indicates presence of a single melting endotherm at 150.8° C. (FIG. 17). TGA thermogram indicates no weight loss (FIG. 18). Based on thermal analysis Form B is confirmed to be an anhydrous polymorph.

TABLE 5

XPRD Peaks of Form B
Form B of Compound (I)

| Angle 2-Theta ° | Relative Intensity % |
|---|---|
| 3.2 ± 0.2 | 12 |
| 10.3 ± 0.2 | 4 |
| 11.2 ± 0.2 | 8 |
| 12.7 ± 0.2 | 97 |
| 15.6 ± 0.2 | 20 |
| 16.4 ± 0.2 | 31 |
| 16.9 ± 0.2 | 27 |
| 17.2 ± 0.2 | 37 |
| 17.8 ± 0.2 | 5 |
| 18.6 ± 0.2 | 69 |
| 19.5 ± 0.2 | 24 |
| 20.0 ± 0.2 | 100 |
| 20.5 ± 0.2 | 37 |
| 21.0 ± 0.2 | 8 |
| 21.4 ± 0.2 | 24 |
| 21.7 ± 0.2 | 36 |
| 22.4 ± 0.2 | 8 |
| 23.1 ± 0.2 | 50 |
| 23.6 ± 0.2 | 13 |
| 23.9 ± 0.2 | 14 |
| 24.6 ± 0.2 | 27 |
| 25.3 ± 0.2 | 48 |
| 25.6 ± 0.2 | 46 |
| 26.8 ± 0.2 | 11 |
| 27.5 ± 0.2 | 4 |
| 28.2 ± 0.2 | 14 |
| 29.5 ± 0.2 | 13 |
| 29.8 ± 0.2 | 7 |
| 30.9 ± 0.2 | 10 |
| 31.8 ± 0.2 | 8 |
| 33.3 ± 0.2 | 12 |
| 34.7 ± 0.2 | 5 |
| 37.1 ± 0.2 | 1 |
| 39.4 ± 0.2 | 4 |
| 40.4 ± 0.2 | 3 |
| 41.5 ± 0.2 | 3 |
| 42.4 ± 0.2 | 1 |
| 43.5 ± 0.2 | 3 |
| 44.7 ± 0.2 | 2 |

TABLE 6

XPRD Peaks of Form C
Form C of Compound (I)

| Angle 2-Theta ° | Relative Intensity % |
|---|---|
| 8.3 ± 0.2 | 20 |
| 10.2 ± 0.2 | 38 |
| 11.4 ± 0.2 | 58 |
| 12.3 ± 0.2 | 45 |
| 14.1 ± 0.2 | 21 |
| 15.2 ± 0.2 | 12 |
| 16.1 ± 0.2 | 43 |
| 16.5 ± 0.2 | 15 |
| 16.8 ± 0.2 | 32 |
| 17.7 ± 0.2 | 8 |
| 18.8 ± 0.2 | 65 |
| 20.3 ± 0.2 | 35 |
| 21.2 ± 0.2 | 100 |
| 22.0 ± 0.2 | 7 |
| 22.7 ± 0.2 | 55 |
| 23.3 ± 0.2 | 12 |
| 23.6 ± 0.2 | 10 |
| 24.6 ± 0.2 | 26 |
| 26.1 ± 0.2 | 25 |
| 26.8 ± 0.2 | 23 |
| 27.4 ± 0.2 | 6 |
| 28.1 ± 0.2 | 28 |
| 28.4 ± 0.2 | 20 |
| 28.9 ± 0.2 | 3 |
| 30.4 ± 0.2 | 11 |
| 30.9 ± 0.2 | 5 |
| 31.4 ± 0.2 | 5 |
| 33.0 ± 0.2 | 5 |
| 33.7 ± 0.2 | 3 |
| 34.3 ± 0.2 | 6 |
| 35.3 ± 0.2 | 2 |
| 36.9 ± 0.2 | 1 |
| 38.4 ± 0.2 | 1 |
| 39.1 ± 0.2 | 2 |
| 41.2 ± 0.2 | 4 |
| 41.8 ± 0.2 | 2 |

Example 14

Preparation of Form C

Compound (I) was prepared according to Example 12 and isolated from concentration of chromatography fractions in chromatographic separation involving initial elution with dichloromethane followed by iPAC/n-heptane. Form C is an IPAc solvate with a desolvation event at 90.12° C. followed by melting at 142.8° C.

Figure 19:
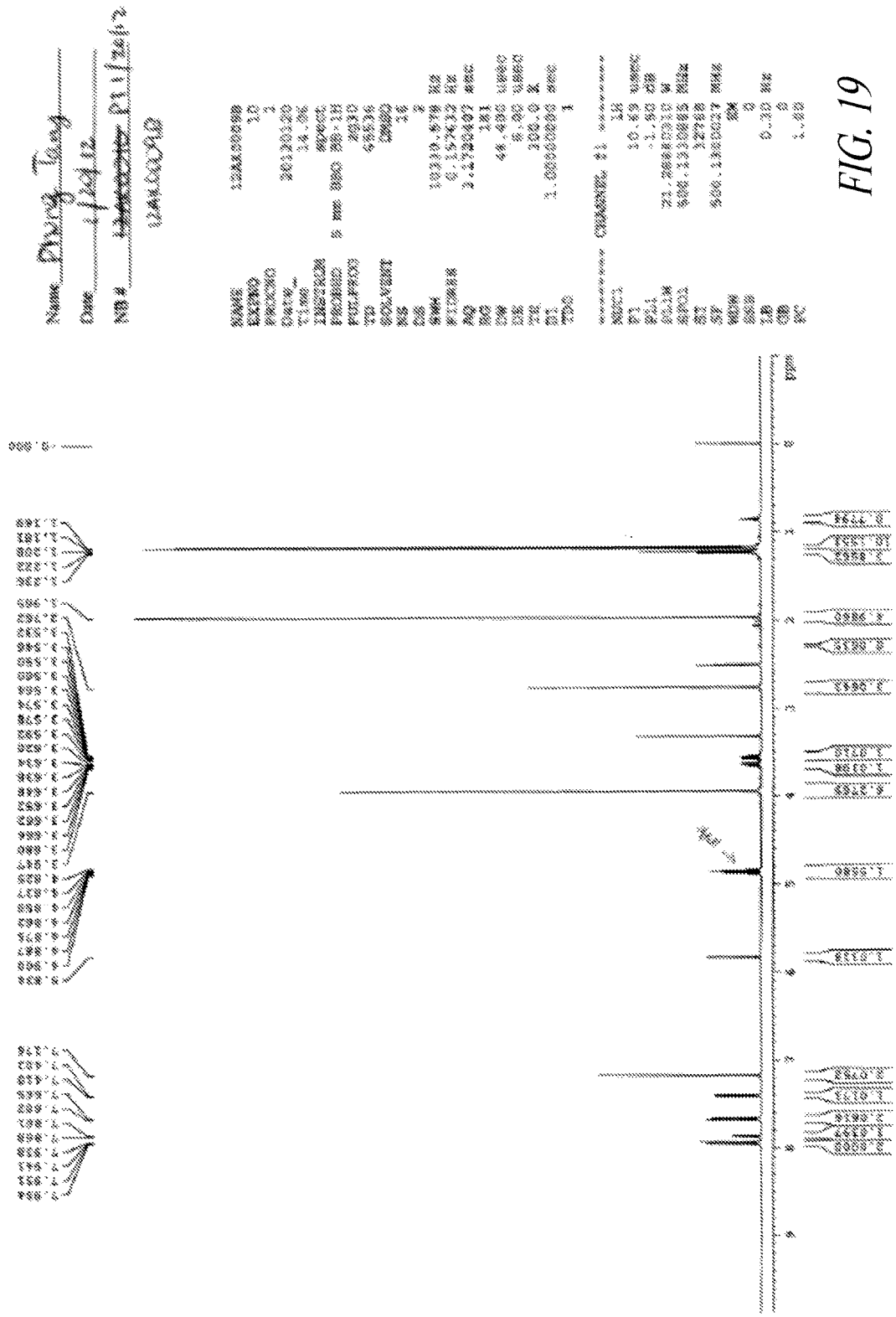
FIG. 19 is the $^1$H NMR of the polymorphic Form C of compound (I).
Figure 20:
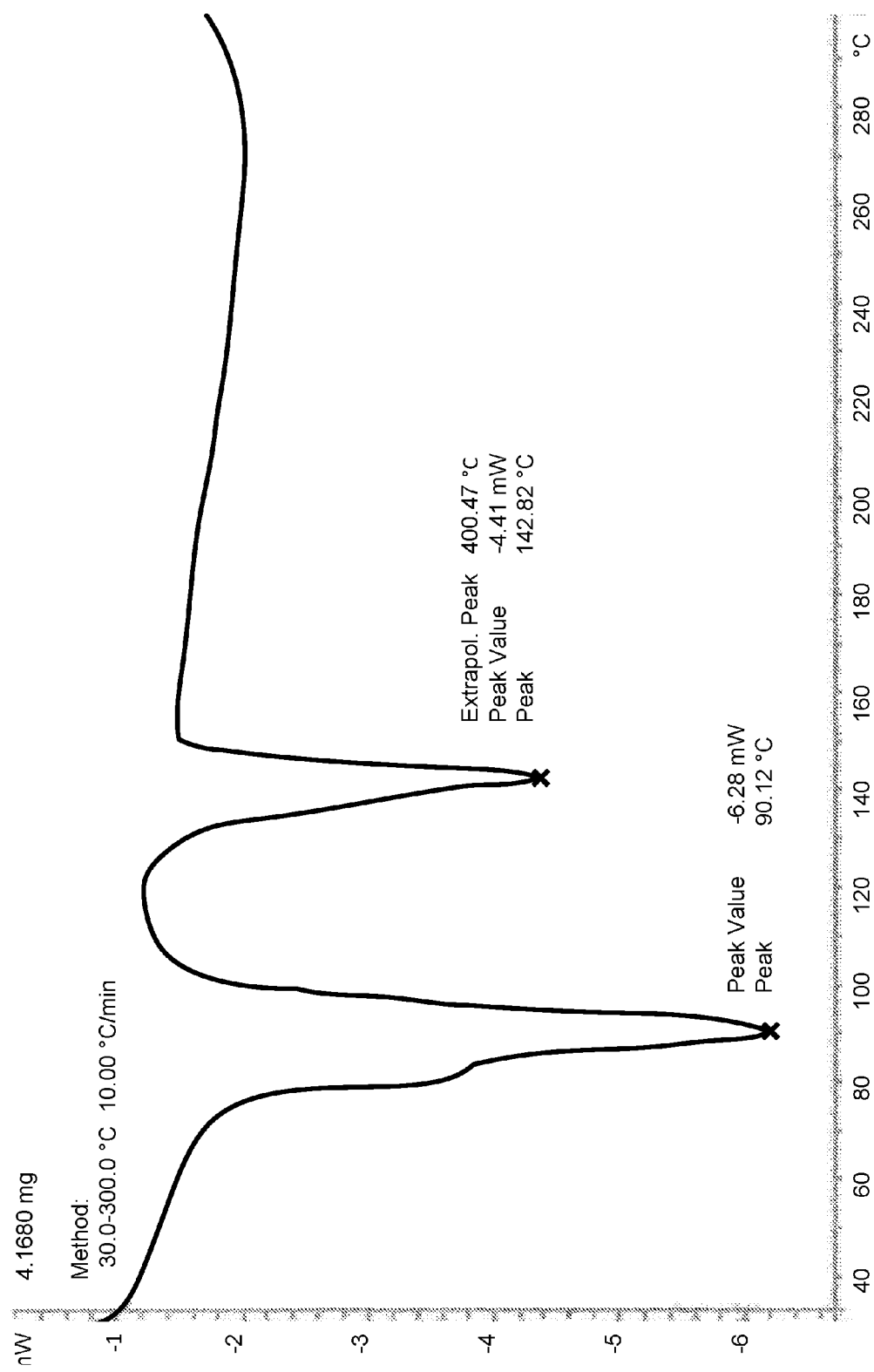
FIG. 20 is the DSC thermogram of the polymorphic Form C of compound (I).

The XRPD pattern of Form C is presented in FIG. 1. $^1$H NMR of this material is consistent with the structure and contains 24.1 wt % residual IPAc (equivalent to 1.5:1 molar ratio of IPAc and Compound (I) (FIG. 19). DSC thermogram of this material indicates two broad endotherms at 90.1° C., corresponding to loss of IPAc and 142.8° C. corresponding to melt (FIG. 20). Therefore, Form C was confirmed to be an IPAc solvate.

Example 15

Preparation of Form D

Compound (I) was spray-dried onto Eudragit polymer at 30% loading. Compound (I) was isolated from the amorphous spray-dried material. Thus, to a reactor was charged 30% Compound (I)-Eudragit product (0.809 kg) and methanol (3.71 L) and the mixture was refluxed for 30 minutes. The mixture was filtered (10 uM filter) and the reactor rinsed with additional methanol (0.825 L). The filtrate was refluxed for 30 minutes then cooled to 50° C. and seeded. The mixture was cooled to room temperature and stirred for 16.5 hours. The solid was isolated on a Buchner filter, rinsed with methanol (2.1 L) twice and dried under vacuum at 45° C. to give Compound (I).

Full chemical analysis of the product showed the potency was 99.2 wt %, 910 ppm residual methanol and 0.16% water (Karl Fischer). Effectively the sample was anhydrous and solvent free. The XRPD spectrum was assigned as Form D.

Figure 21:
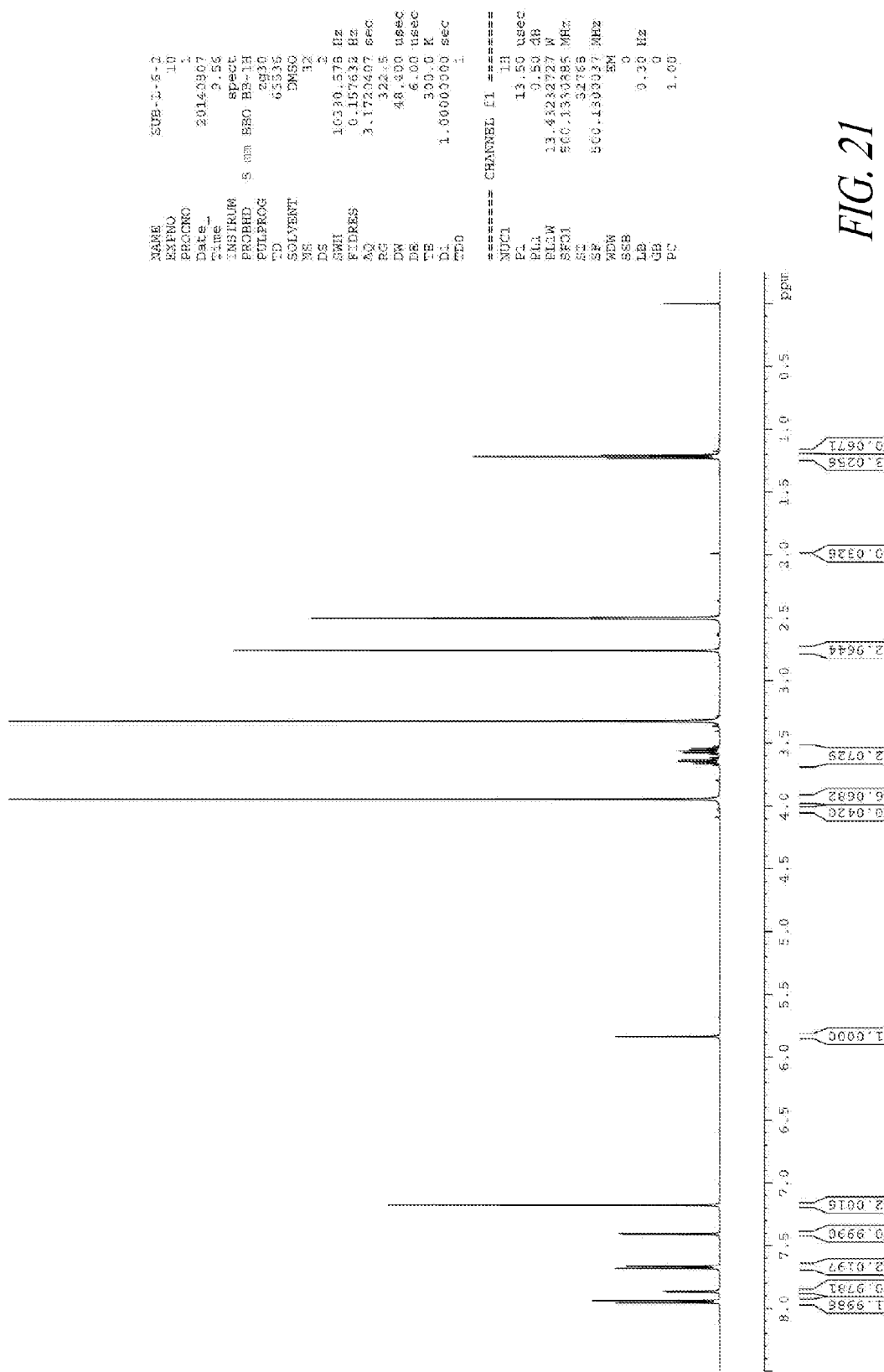
FIG. 21 is the $^1$H NMR of the polymorphic Form D of compound (I).
Figure 22:
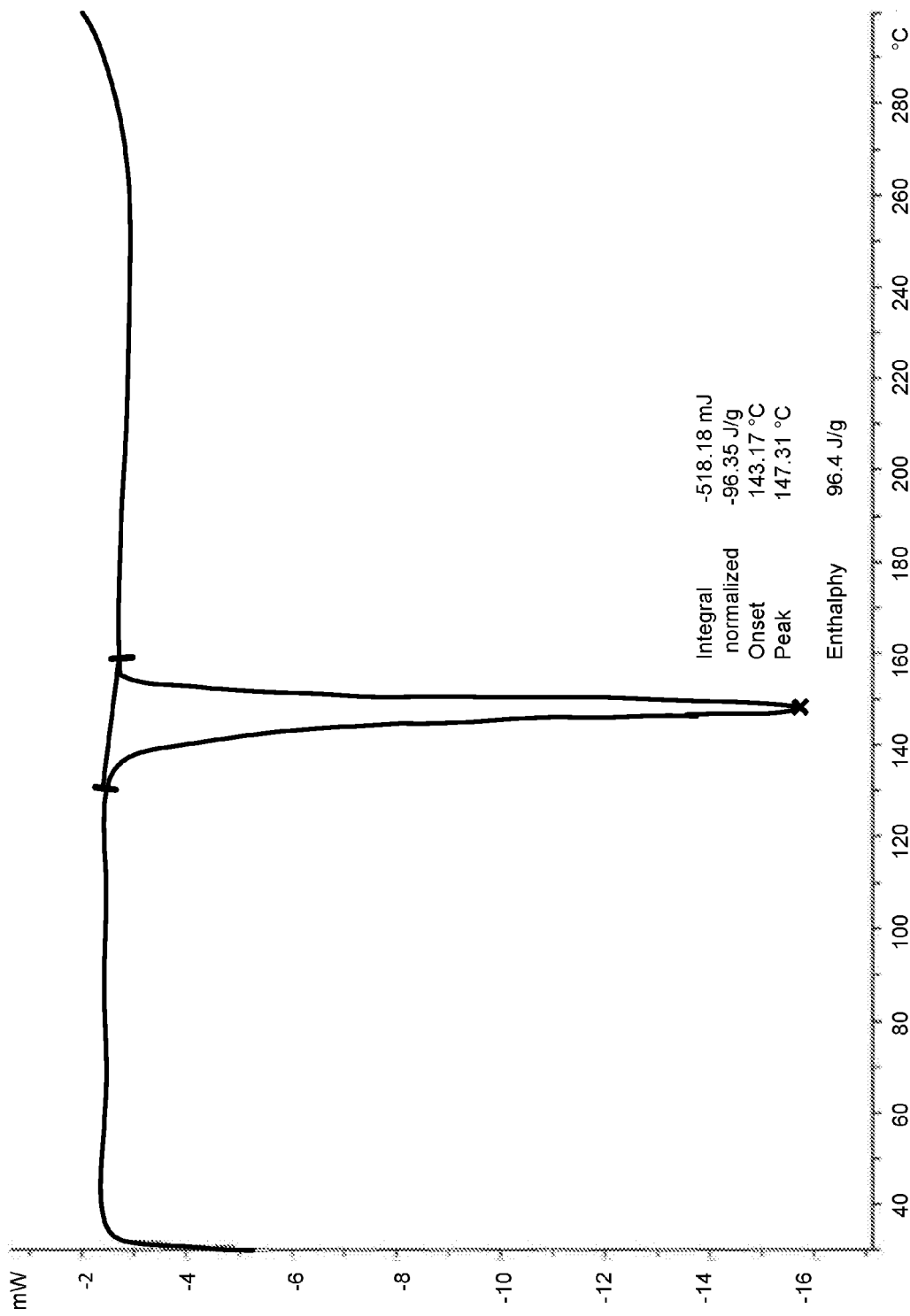
FIG. 22 is the DSC thermogram of the polymorphic Form D of compound (I).
Figure 23:
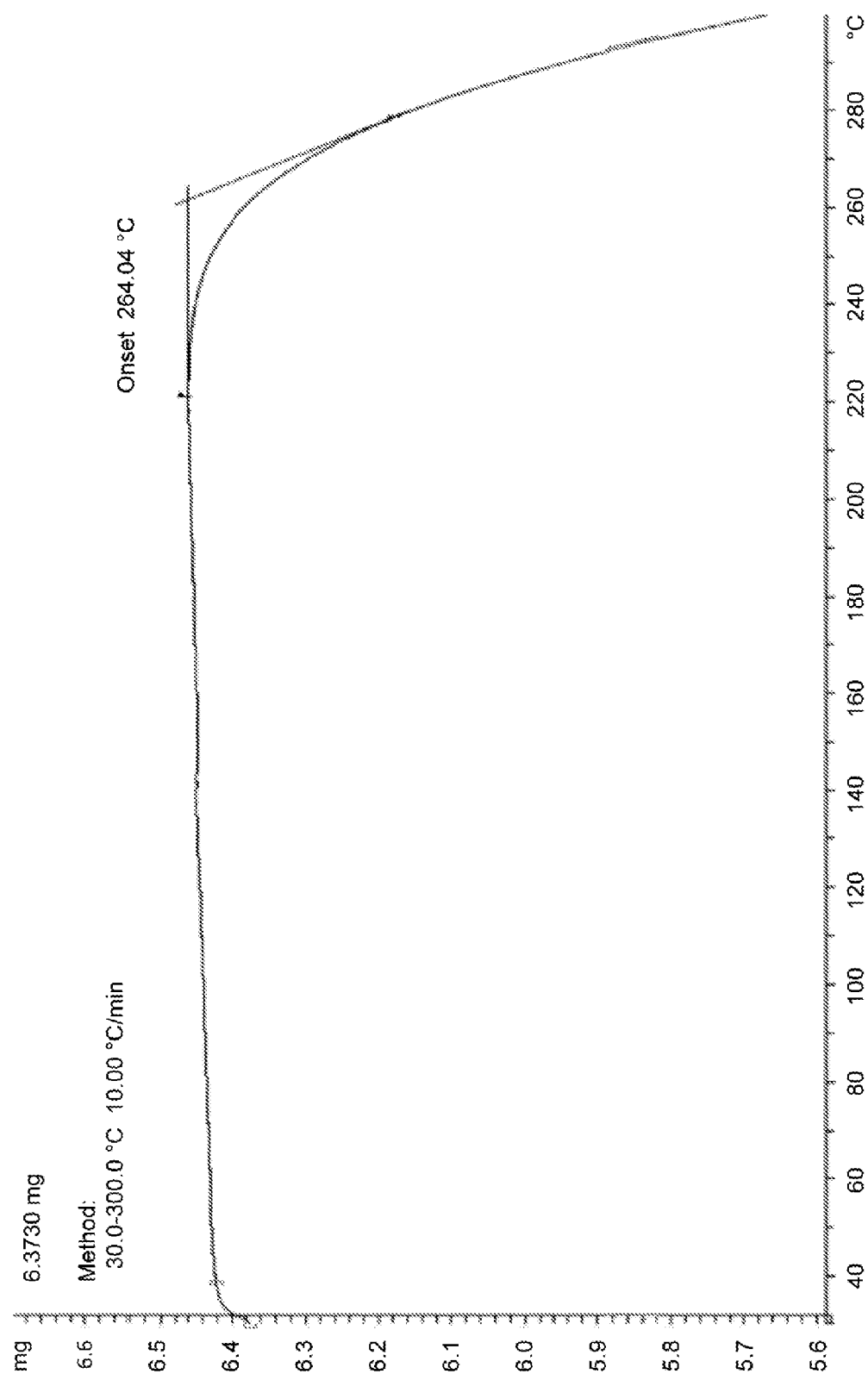
FIG. 23 is the TGA thermogram of the polymorphic Form D of compound (I).

XRPD pattern of Form D is presented in FIG. 1. Additional Form D material was generated by slurrying Form F material in EtOAc with Form D seeds at 50° C. Material obtained from this slurry was used for further characterization of Form D. $^1$H NMR of Form D is consistent with the structure and contains 0.2 wt % EtOAc (FIG. 21). DSC thermogram shows a single melting transition at 147.3° C. (FIG. 22). TGA shows no weight loss (FIG. 23).

Example 16

Preparation of Form E

Figure 29:
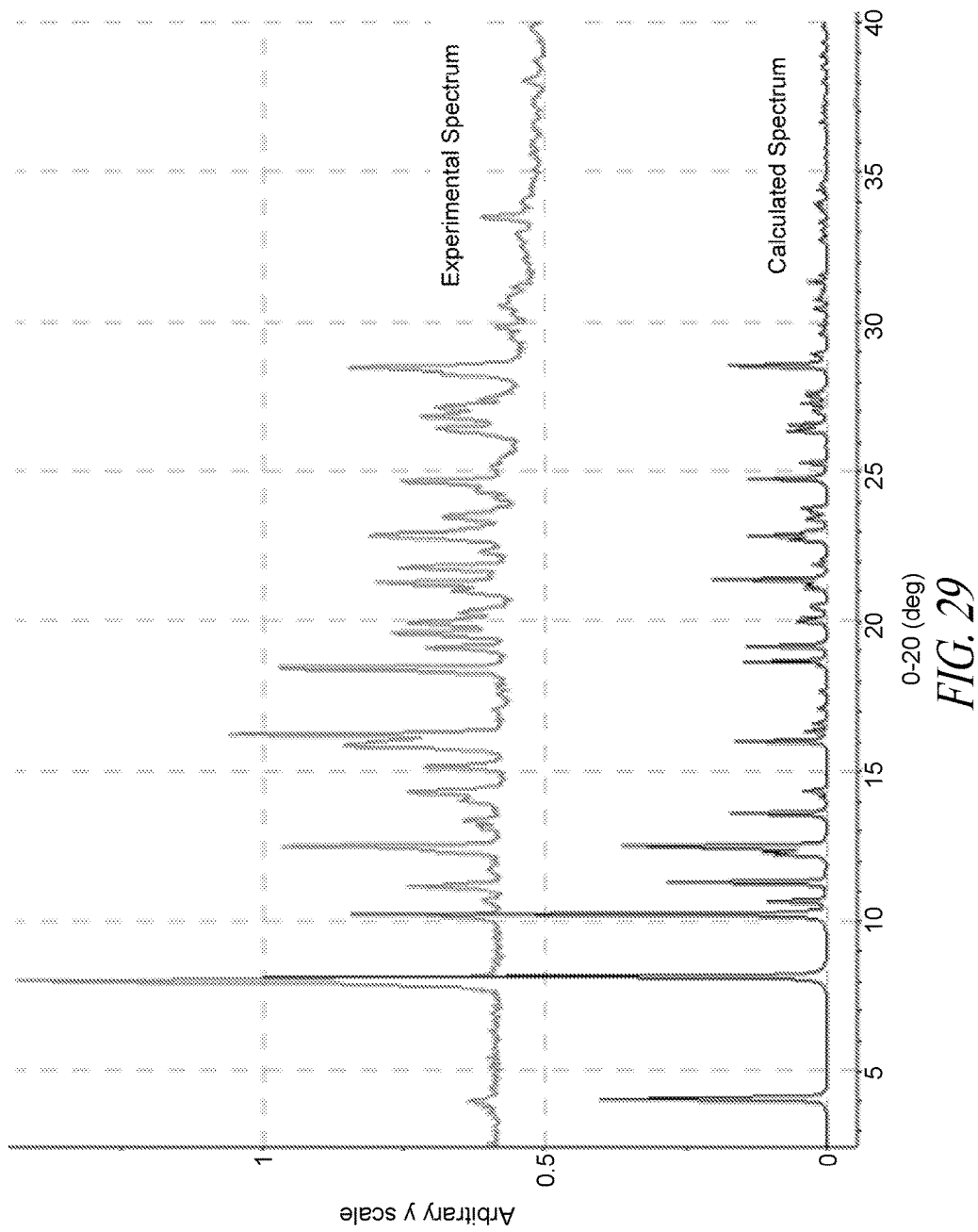
FIG. 29 is the experimental XRPD pattern of the polymorphic Form E of compound (I) (upper) and the calculated XRPD pattern of the polymorphic Form E of compound (I) (lower).

Compound (I) was prepared according to the general procedures found in International PCT Application Publication No. WO 2011/112828. Crystals suitable for single crystal X-ray analysis were obtained by slow cooling from ~64° C. to ~34° C. of Compound (I) dissolved in 1:1 heptane:THF, crystalline Form A. The single crystal structural data indicated the solid was a solvated form of Compound (I) containing THF although the exact stoichiometry and nature of the solvate could not be determined due to disorder. Proton NMR for the material indicated the presence of ~0.5 moles of THF and ~0.2 moles of heptane. The XRPD spectrum generated from the atomic coordinates, space group and unit cell parameters of the single crystal was unique and did not match that of a previous bulk sample. Thus, although the crystallization solution was seeded with Compound (I) Form A crystals, a different, THF solvated, form of Compound (I) crystallized from solution. The unique XRPD spectral pattern associated with the THF solvate was assigned crystal Form E (FIG. 29).

TABLE 7

XPRD Peaks of Form E
Form E of Compound (I)

| Angle 2-Theta ° | Relative Intensity % |
|---|---|
| 4.0 ± 0.2 | 20 |
| 8.0 ± 0.2 | 100 |
| 10.2 ± 0.2 | 27 |
| 10.7 ± 0.2 | 18 |
| 11.2 ± 0.2 | 29 |
| 11.7 ± 0.2 | 17 |
| 12.5 ± 0.2 | 51 |
| 13.1 ± 0.2 | 18 |
| 13.4 ± 0.2 | 21 |
| 14.0 ± 0.2 | 22 |
| 14.3 ± 0.2 | 31 |
| 15.2 ± 0.2 | 28 |
| 15.8 ± 0.2 | 42 |
| 16.0 ± 0.2 | 38 |
| 16.2 ± 0.2 | 61 |
| 18.4 ± 0.2 | 54 |
| 19.1 ± 0.2 | 28 |
| 19.6 ± 0.2 | 34 |
| 19.9 ± 0.2 | 31 |
| 20.3 ± 0.2 | 21 |
| 21.0 ± 0.2 | 23 |
| 21.3 ± 0.2 | 36 |
| 21.8 ± 0.2 | 32 |
| 22.3 ± 0.2 | 18 |
| 22.9 ± 0.2 | 38 |
| 23.5 ± 0.2 | 24 |
| 24.1 ± 0.2 | 16 |
| 24.4 ± 0.2 | 19 |
| 24.7 ± 0.2 | 31 |
| 26.4 ± 0.2 | 26 |
| 26.8 ± 0.2 | 29 |
| 27.2 ± 0.2 | 26 |
| 27.4 ± 0.2 | 18 |
| 28.5 ± 0.2 | 41 |

Example 17

Preparation of Form G

A clear yellow solution consisting of 80.4 mg of Compound (I) and 1 mL of chloroform was prepared. The solution was filtered into a new clean vial using 0.2 μm nylon syringe filter. The vial was placed uncapped into a larger vial containing 10 mL of isopropyl ether. The larger vial was capped and stored 4 days at room temperature for vapor diffusion. Large yellow solids were observed in the small vial. The small vial was removed from the larger vial, the solution was decanted, and solids allowed to dry at room temperature.

Figure 30:
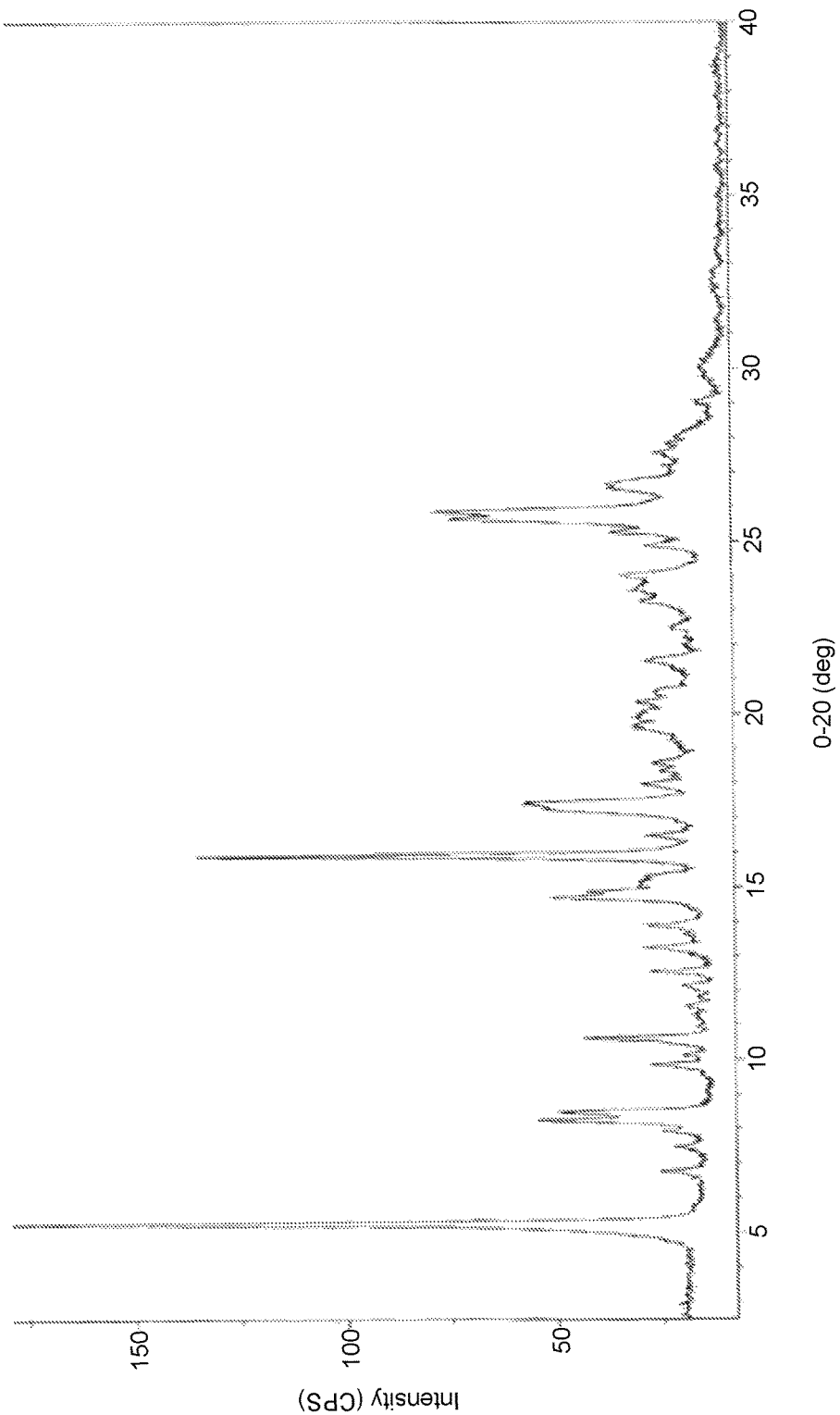
FIG. 30 is the X-ray powder diffraction (XRPD) pattern of the polymorphic Form G of compound (I).

The material exhibited a unique XRPD spectrum that was assigned as Form G (FIG. 30). Thermal analysis was consistent with a solvated or hydrated material possibly a monohydrate. Only trace amounts of the crystallization solvents were observed in the proton NMR spectrum suggesting that the sample is actually a hydrate. The DSC showed two thermal events, one at 115.6° C. and a second at 146.9° C. suggestive of melting. TGA analysis showed a 3.7% weight loss primarily associated with the initial thermal event. The material was found to be metastable converting to Form F on slurrying in water or 1:1 acetone:water at room temperature.

TABLE 8

XPRD Peaks of Form G
Form G of Compound (I)

| Angle 2-Theta ° | Relative Intensity % |
|---|---|
| 5.3 ± 0.2 | 100 |
| 6.8 ± 0.2 | 14 |
| 7.5 ± 0.2 | 12 |
| 7.9 ± 0.2 | 14 |
| 8.2 ± 0.2 | 30 |
| 8.5 ± 0.2 | 27 |
| 9.9 ± 0.2 | 15 |
| 10.1 ± 0.2 | 11 |
| 10.6 ± 0.2 | 24 |
| 11.5 ± 0.2 | 11 |
| 12.2 ± 0.2 | 10 |
| 12.6 ± 0.2 | 15 |
| 13.2 ± 0.2 | 16 |
| 13.9 ± 0.2 | 16 |
| 14.7 ± 0.2 | 28 |
| 14.9 ± 0.2 | 23 |
| 15.9 ± 0.2 | 74 |
| 16.5 ± 0.2 | 16 |
| 17.3 ± 0.2 | 28 |
| 17.4 ± 0.2 | 31 |
| 18.0 ± 0.2 | 16 |
| 18.4 ± 0.2 | 13 |
| 18.6 ± 0.2 | 14 |
| 20.4 ± 0.2 | 17 |
| 21.6 ± 0.2 | 16 |
| 22.5 ± 0.2 | 12 |
| 23.3 ± 0.2 | 16 |
| 24.0 ± 0.2 | 19 |
| 24.9 ± 0.2 | 15 |
| 25.3 ± 0.2 | 20 |
| 25.7 ± 0.2 | 41 |
| 25.9 ± 0.2 | 43 |
| 26.6 ± 0.2 | 20 |

It will be appreciated that, although specific embodiments of the invention have been described herein for purposes of illustration, various modifications may be made without departing from the spirit and scope of the invention. Accordingly, the invention is not limited except as by the appended claims.

What is claimed is:

1. A crystalline hydrate of Compound (I)

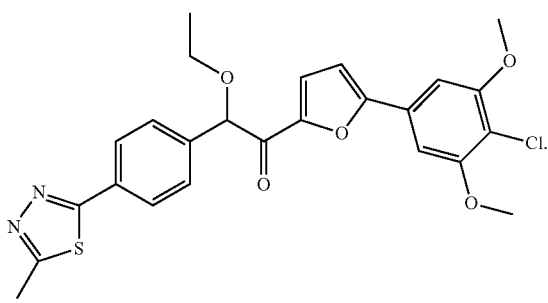

having a primitive monoclinic lattice Bravais type.

2. The crystalline hydrate of Compound (I) according to claim 1 wherein the primitive monoclinic lattice comprises vectors wherein a is about 8.655 Å, α is about 90°, b is about 17.893 Å, β is about 102.67°, c is about 16.315 Å, and γ is about 90°.

3. The crystalline hydrate of Compound (I) according to claim 1 having a space group of $P2_1/c$.

4. A crystalline hydrate of Compound (I)

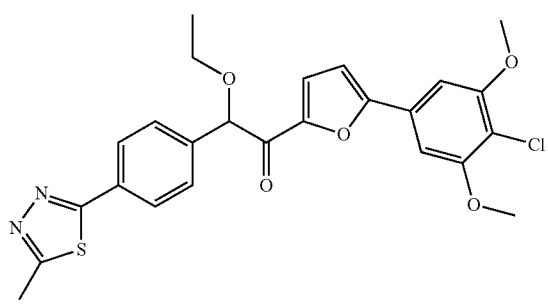

having an X-ray powder diffraction pattern comprising peaks at 9.9, 12.2, and 14.9 degrees 2θ (±0.2 degrees 2θ) when measured using CuKα radiation.

5. The crystalline hydrate of Compound (I) according to claim 4 having an X-ray powder diffraction pattern further comprising peaks at 10.4, 19.5, 20.1, 22.5, 22.9, and 25.8 degrees 2θ (±0.2 degrees 2θ) when measured using CuKα radiation.

6. The crystalline hydrate of Compound (I) according to claim 4 having an X-ray powder diffraction pattern substantially the same as that shown in FIG. 24.

7. The crystalline hydrate of Compound (I) according to claim 4 having a DSC thermogram substantially the same as that shown in FIG. 5.

8. The crystalline hydrate of Compound (I) according to claim 4 having a TGA curve substantially the same as that shown in FIG. 6.

9. The crystalline hydrate of Compound (I) according to claim 4 having a dynamic vapor sorption isotherm substantially the same as that shown in FIG. 7.

10. A crystalline hydrate of Compound (I)

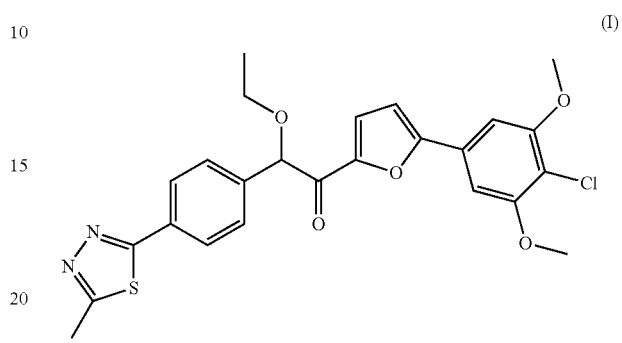

having an X-ray powder diffraction pattern substantially the same as shifted Form F in FIG. 1.

11. The crystalline hydrate of Compound (I) according to claim 10 having a dynamic vapor sorption isotherm substantially the same as that shown in FIG. 9.

12. The crystalline hydrate of Compound (I) according to claim 10 having a DSC thermogram substantially the same as that shown in FIG. 10.

13. The crystalline hydrate of Compound (I) according to claim 10 having a TGA curve substantially the same as that shown in FIG. 11.

14. A pharmaceutical composition comprising a crystalline hydrate according to any one of claim 1, 4, or 10, and at least one pharmaceutically acceptable carrier or diluent.

15. A method for inhibiting PDE10 in a warm-blooded animal, comprising administering to the animal an effective amount of a pharmaceutical composition according to claim 14.

16. A method for treating a neurological disorder in a warm-blooded animal having said neurological disorder, comprising administering to the animal an effective amount of pharmaceutical composition according to claim 14, wherein the neurological disorder is selected from the group consisting of psychotic disorders, anxiety disorders, Parkinson's disease, Huntington's disease, Alzheimer's disease, encephalitis, phobias, epilepsy, aphasia, Bell's palsy, cerebral palsy, sleep disorders, pain, Tourette's syndrome, schizophrenia, delusional disorders, bipolar disorders, post-traumatic stress disorders, drug-induced psychosis, panic disorders, obsessive-compulsive disorders, attention-deficit disorders, disruptive behavior disorders, autism, depression, dementia, epilepsy, insomnias and multiple sclerosis.

17. The method of claim 16 wherein the neurological disorder is schizophrenia.

18. The method of claim 16 wherein the neurological disorder is Huntington's disease.

* * * * *